(12) United States Patent
Cho et al.

(10) Patent No.: US 10,100,006 B2
(45) Date of Patent: Oct. 16, 2018

(54) COMPOUND HAVING IMMUNE DISEASE TREATMENT EFFECT AND USE THEREOF

(71) Applicant: THE CATHOLIC UNIVERSITY OF KOREA INDUSTRY—ACADEMIC COOPERATION FOUNDATION, Seoul (KR)

(72) Inventors: Mi-La Cho, Seoul (KR); Dong-Yun Shin, Seoul (KR); Sung-Hwan Park, Seoul (KR); Chul-Woo Yang, Seoul (KR); Jong-Young Choi, Seoul (KR); Min-Jung Park, Seoul (KR); Hye-Jin Son, Seoul (KR); Sung-Hee Lee, Seoul (KR); Seon-Yeong Lee, Seoul (KR); Eun-Kyung Kim, Seoul (KR); Jae-Kyung Kim, Seoul (KR); Seung-Hun Lee, Gwacheon-si (KR); Seong-Hyeok Park, Yeongju-si (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/819,758

(22) Filed: Nov. 21, 2017

(65) Prior Publication Data

US 2018/0118668 A1 May 3, 2018

Related U.S. Application Data

(60) Division of application No. 15/339,410, filed on Oct. 31, 2016, now abandoned, which is a continuation-in-part of application No. PCT/KR2015/004299, filed on Apr. 29, 2015.

(30) Foreign Application Priority Data

Apr. 29, 2014 (KR) .................. 10-2014-0051261
Apr. 29, 2015 (KR) .................. 10-2015-0060182

(51) Int. Cl.
C07C 279/18 (2006.01)

(52) U.S. Cl.
CPC .................. *C07C 279/18* (2013.01)

(58) Field of Classification Search
None
See application file for complete search history.

(56) References Cited

U.S. PATENT DOCUMENTS

| | | | |
|---|---|---|---|
| 7,622,117 B2 | 11/2009 | Tobia et al. | |
| 7,671,019 B2 | 3/2010 | Tobia et al. | |
| 7,749,503 B2 | 7/2010 | Tobia et al. | |
| 2003/0219440 A1 | 11/2003 | Tobia et al. | |
| 2005/0159383 A1 | 7/2005 | Tobia et al. | |
| 2008/0292568 A1 | 11/2008 | Tobia et al. | |
| 2010/0310482 A1 | 12/2010 | Tobia et al. | |
| 2011/0053941 A1 | 3/2011 | Mautino et al. | |
| 2012/0283299 A1 | 11/2012 | Kim et al. | |
| 2012/0309799 A1 | 12/2012 | Kim et al. | |
| 2013/0095140 A1 | 4/2013 | Baron et al. | |
| 2015/0238445 A1 | 8/2015 | Cho et al. | |
| 2017/0157069 A1 | 6/2017 | Cho et al. | |

FOREIGN PATENT DOCUMENTS

| | | |
|---|---|---|
| KR | 10-2011-0053837 A | 5/2011 |
| KR | 10-2011-0081095 A | 7/2011 |
| KR | 10-2014-0036598 A | 3/2014 |
| WO | 03/089601 A2 | 10/2003 |

OTHER PUBLICATIONS

Chemical Abstract Registry No. 1555308-85-4, indexed in the Registry File on STN CAS Online Feb. 25, 2014.

*Primary Examiner* — Po-Chih Chen
(74) *Attorney, Agent, or Firm* — Vorys, Sater, Seymour & Pease LLP; Mih Suhn Koh

(57) ABSTRACT

Provided is a novel compound capable of effectively preventing and treating immune diseases and a use thereof. The novel compound of the present subject matter has effects of inhibiting the production of inflammatory cytokines, increasing the activity of regulatory T cells having immunoregulatory functions, inhibiting the production of autoantibodies to regulate excessive immune responses, and inhibiting the differentiation of osteoclasts, and thus can be used for treating immune diseases, such as autoimmune disease, inflammatory disease, and transplant rejection diseases, which are caused by abnormal regulation of various kinds of immune response.

8 Claims, 36 Drawing Sheets
(21 of 36 Drawing Sheet(s) Filed in Color)

Autoantibody production and immune response regulation

Differentiation inhibition regulation of osteoclasts

FIG 3C
Inflammatory cytokine production regulation
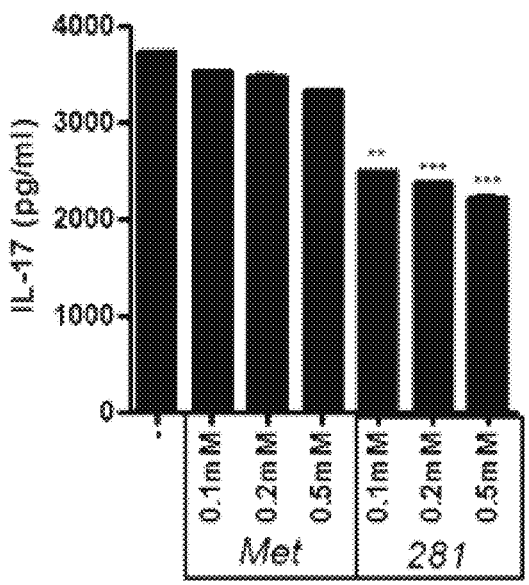
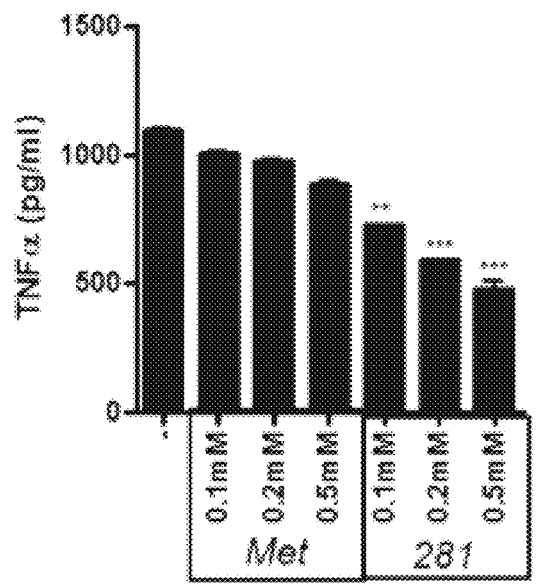
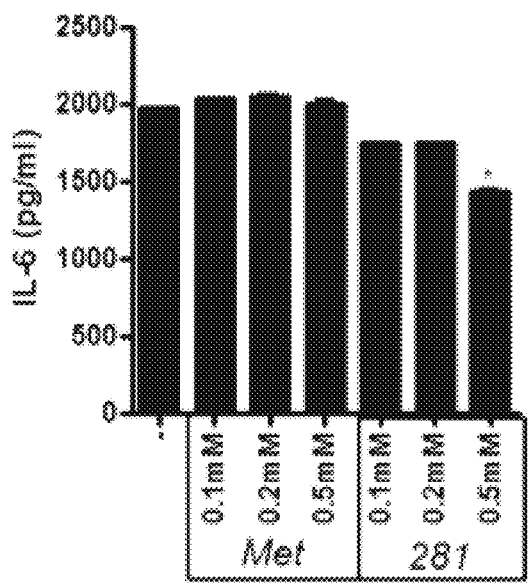
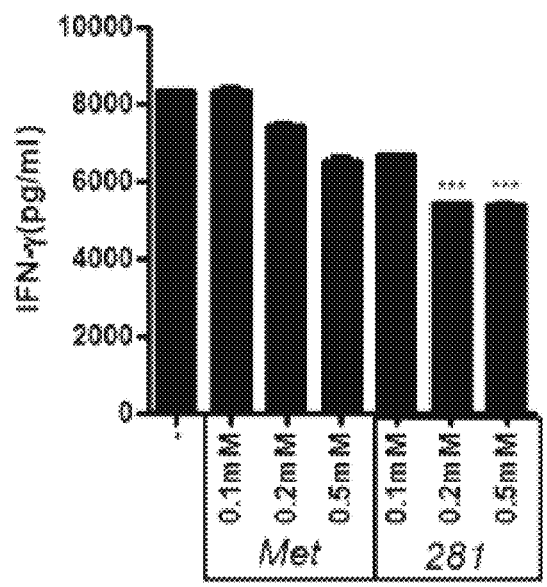

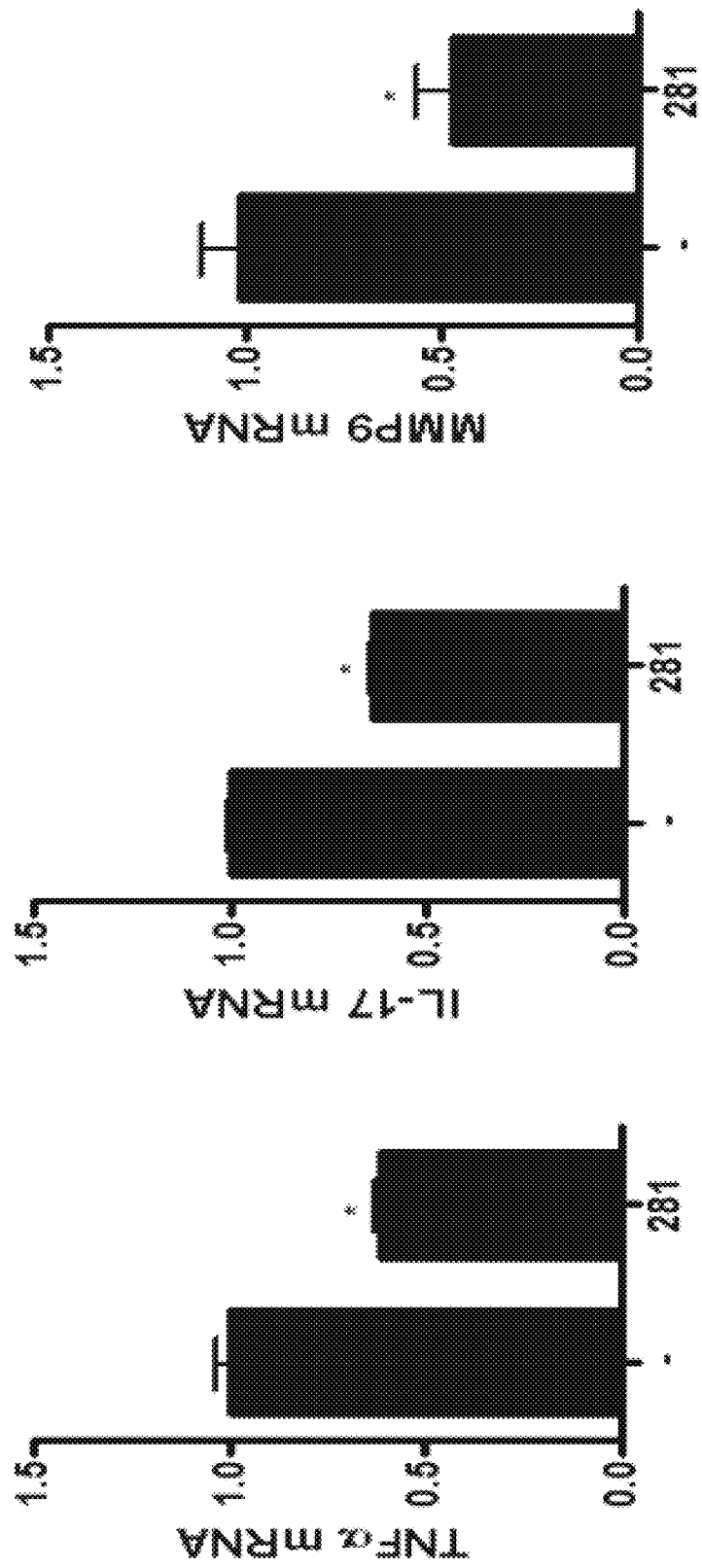

Simultaneous regulation effect of Th17 inhibition/ Treg cell induction

FIG 4B
Differentiation inhibition regulation
Of osteoclast
control
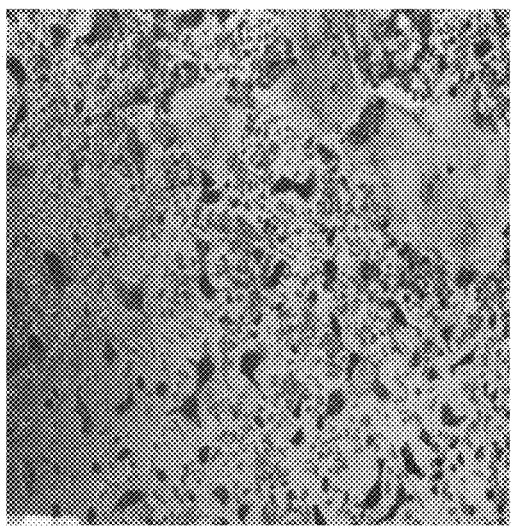
SD281
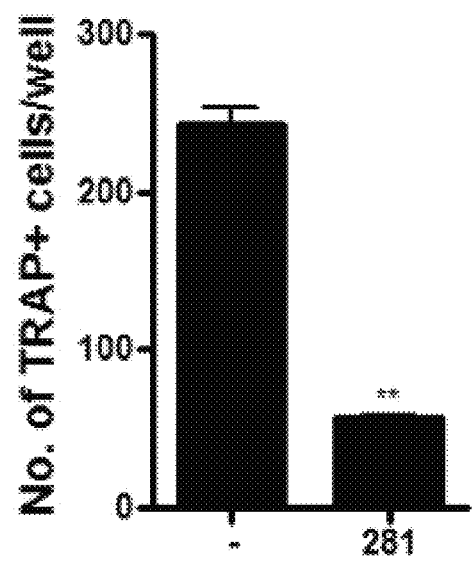

Cytotoxic effect regulation(MTT assay)

Inflammatory cytokine production regulation

Autoantibody production and immune response regulation

Inflammatory gene factor regulation

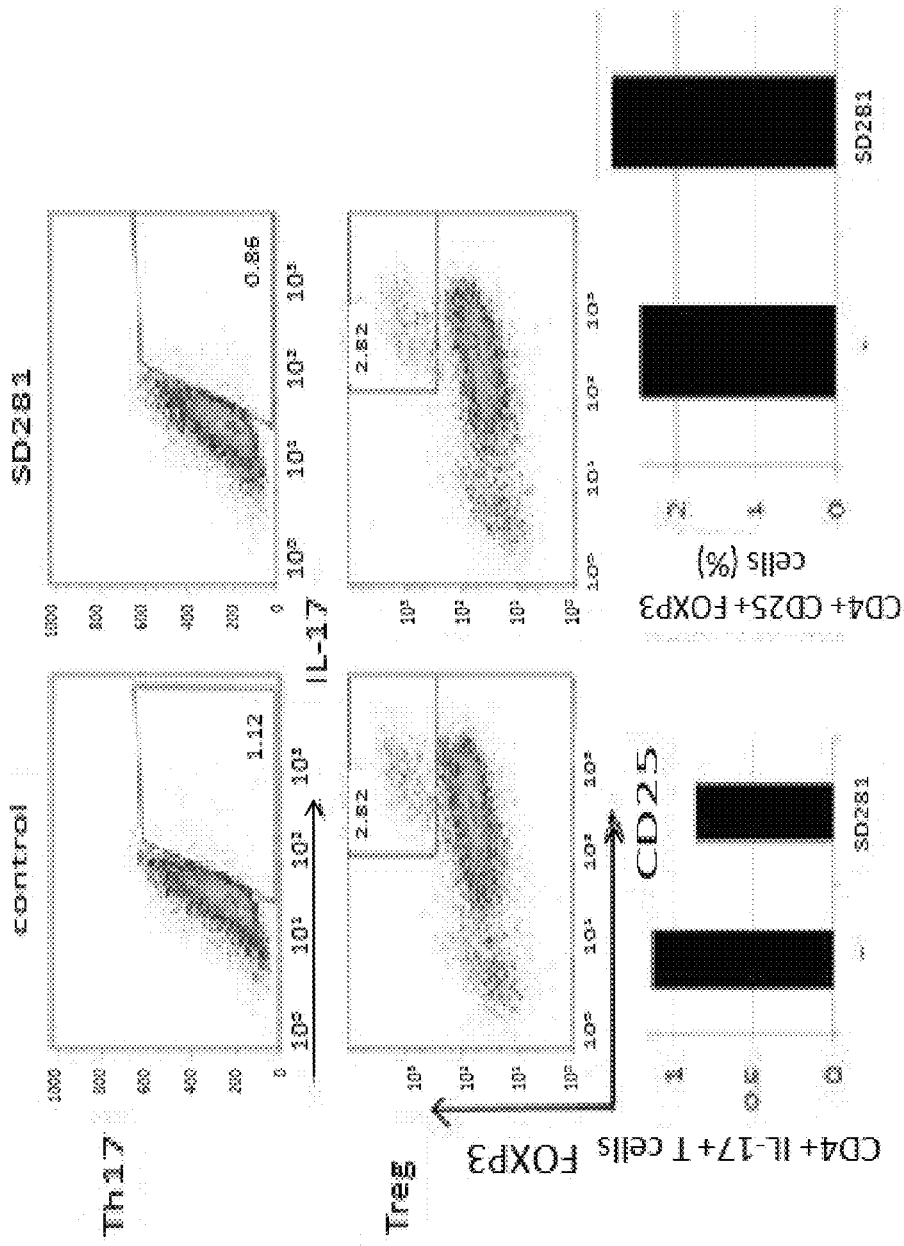

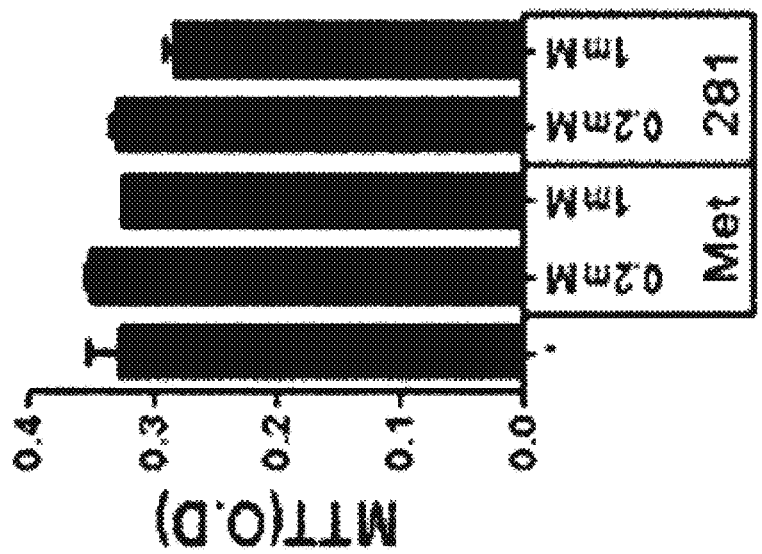

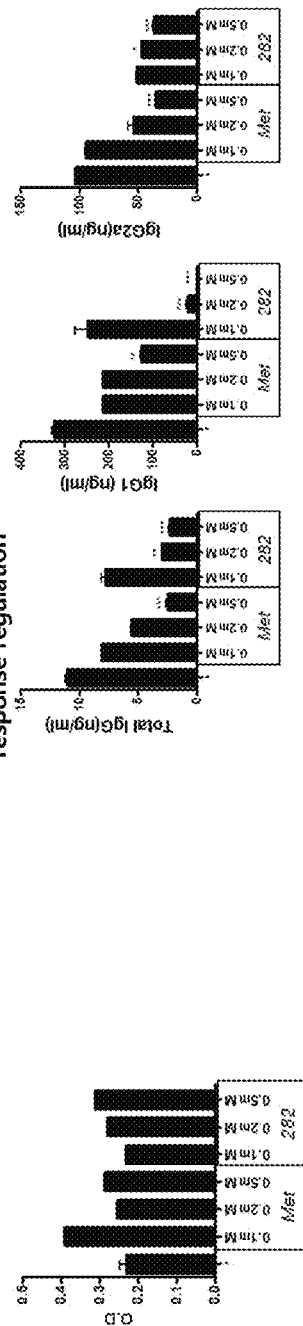
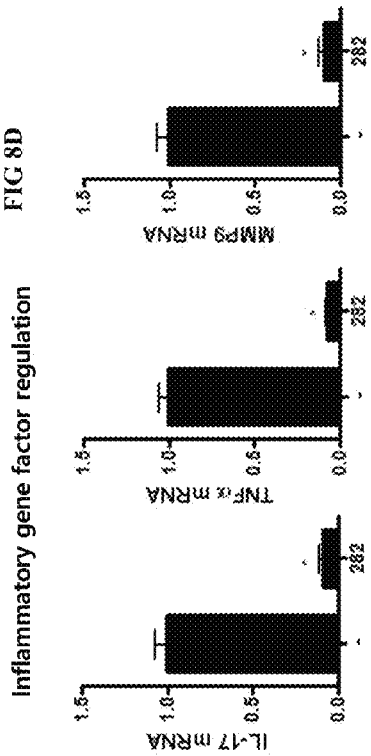
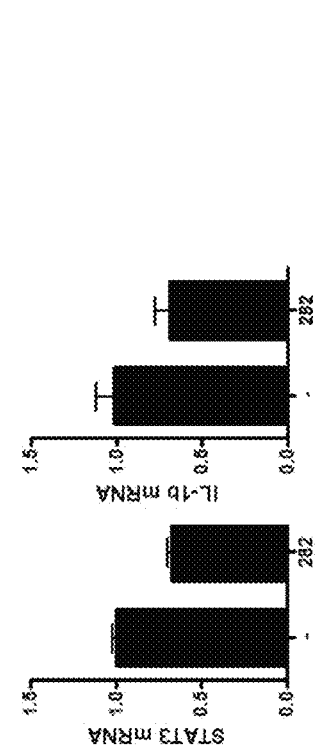
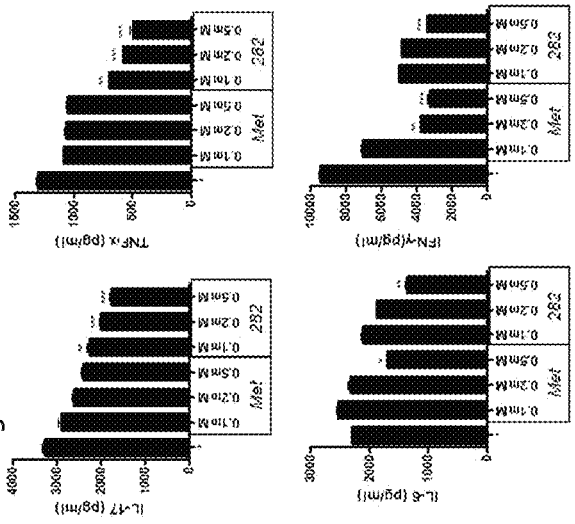
FIG 8A Cytotoxic effect regulation (MTT assay)
FIG 8B Autoantibody production and immune response regulation
FIG 8C Inflammatory cytokine production regulation
FIG 8D Inflammatory gene factor regulation

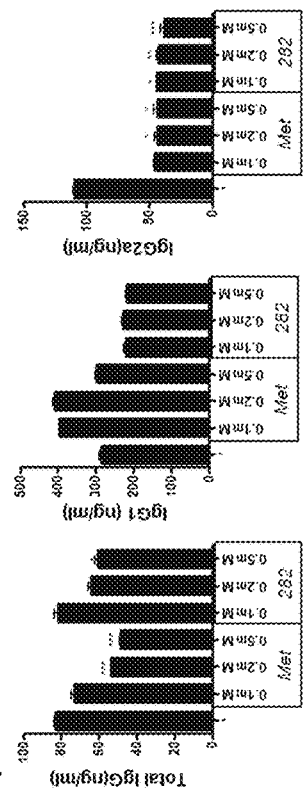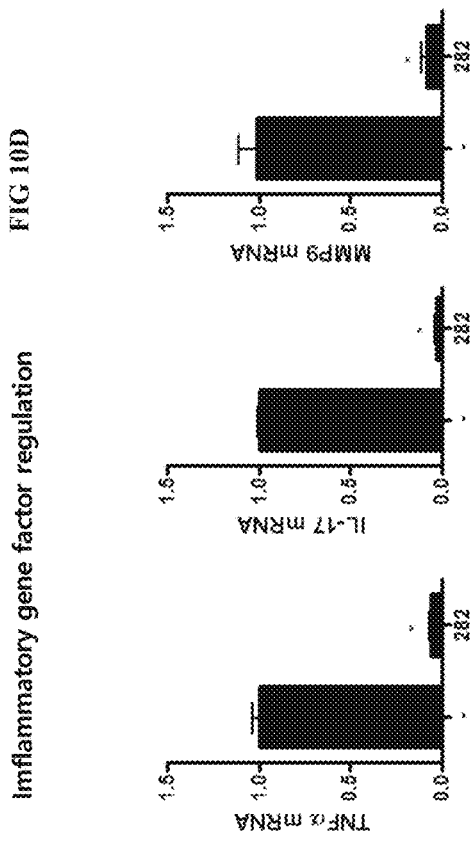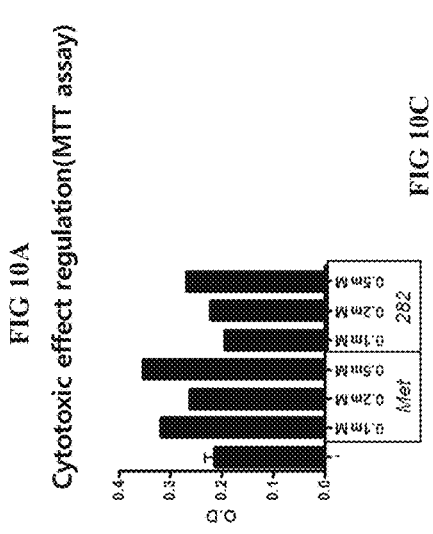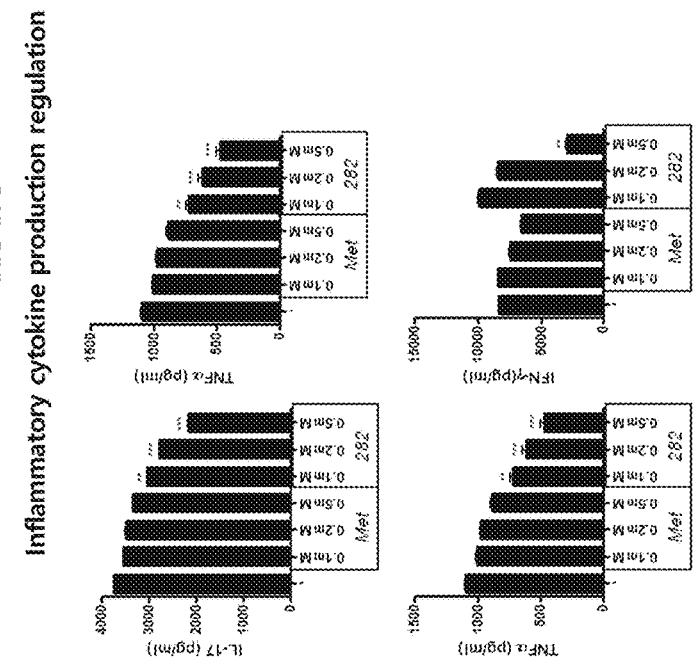
FIG 10A Cytotoxic effect regulation (MTT assay)
FIG 10B Autoantibody production and immune response
FIG 10C Inflammatory cytokine production regulation
FIG 10D Inflammatory gene factor regulation Diffentiation inhibition regulation of osteoclasts Simultaneous regulation effect of Th17 inhibition /Treg cell induction

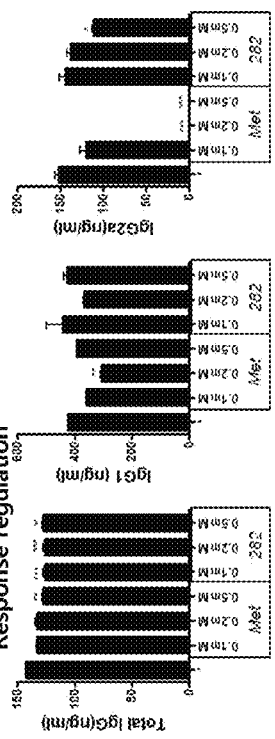
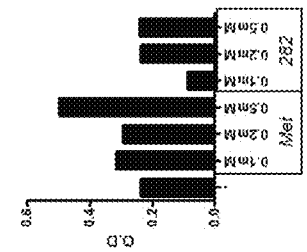
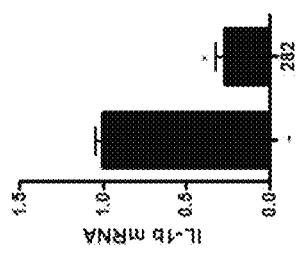
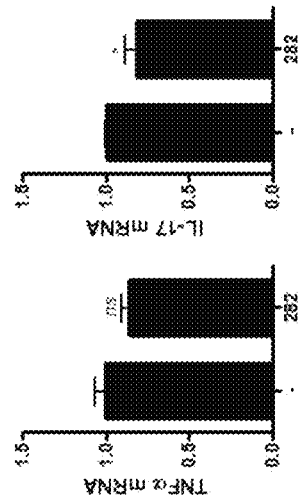
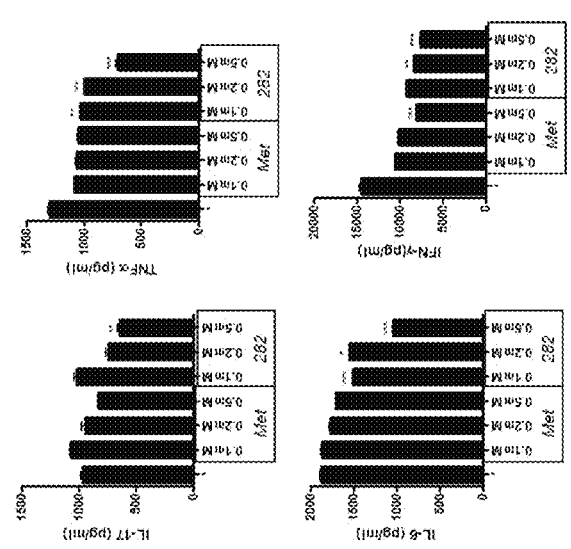
FIG 12A Cytotoxic effect regualtion (MTT assay)
FIG 12B Autoantibody production and immune Response regulation
FIG 12C Inflammatory cytokine production regulation
FIG 12D Inflammatory gene factor regulation FIG 14A  Cytotoxic effect regulation(MTT assay)
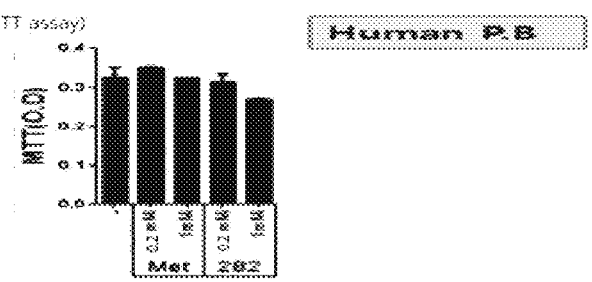
FIG 14B  Inflammatory cytokine production regulation
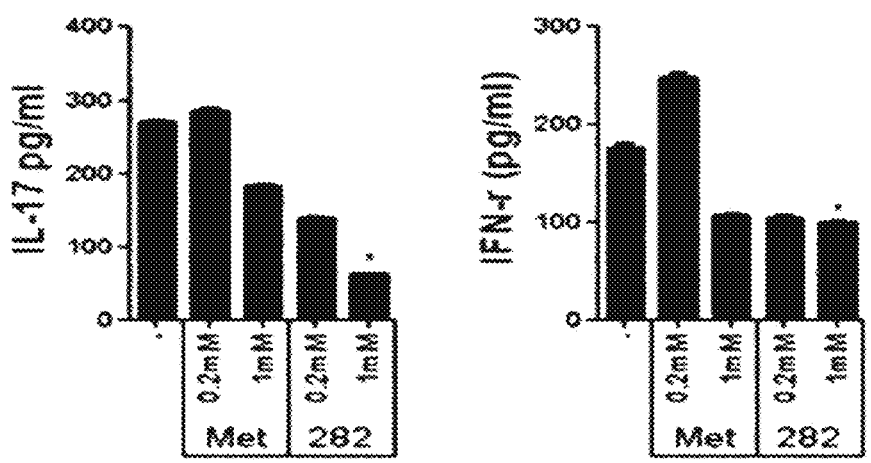

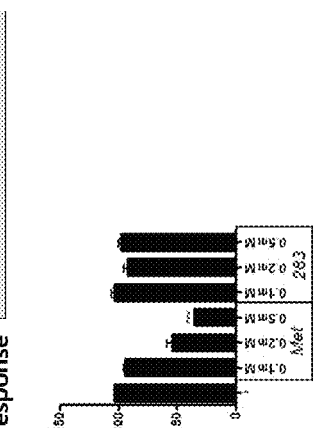
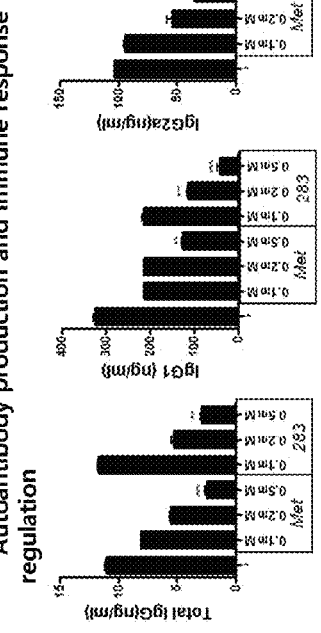
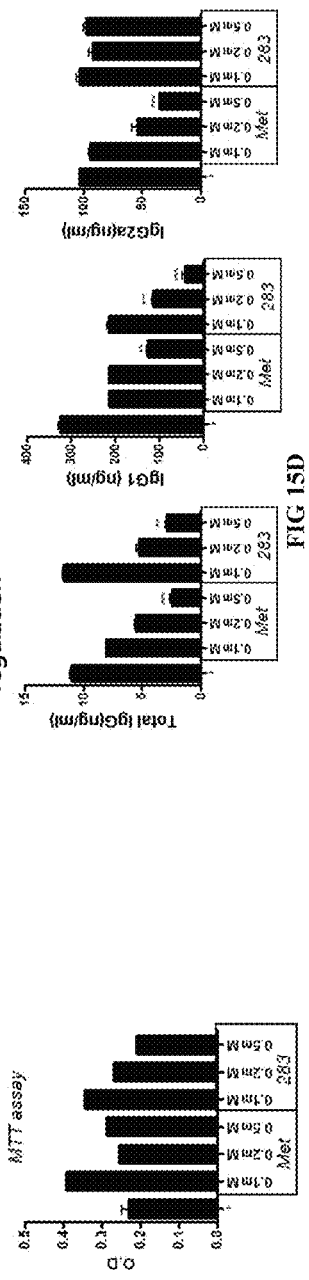
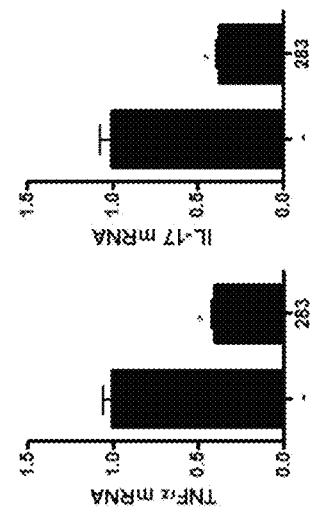
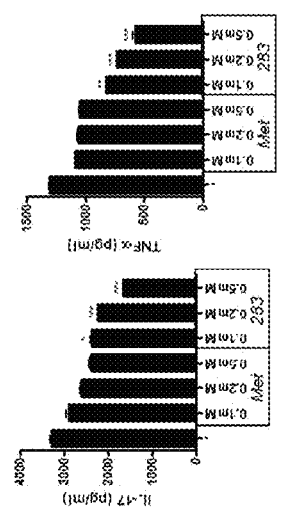
FIG 15A Cytotoxic effect regulation (MTT assay)
FIG 15B Autoantibody production and immune response regulation
FIG 15C Inflammatory cytokine production regulation
FIG 15D Inflammatory gene factor regualtion
Nomal mouse cell

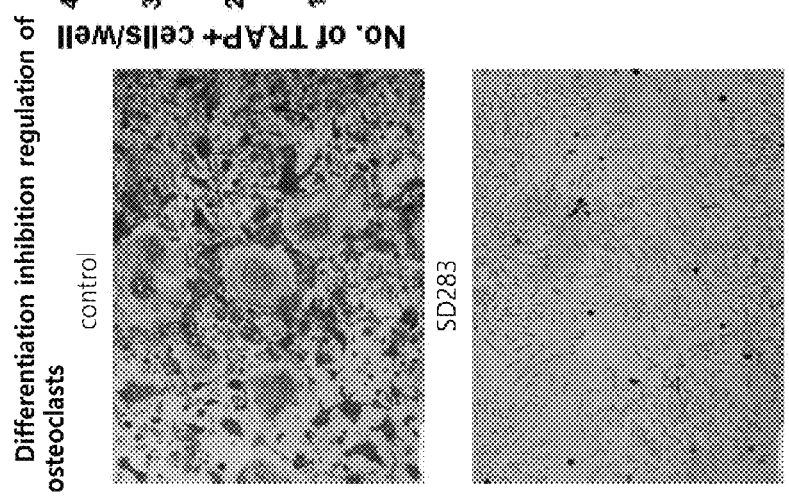
FIG 16B Differentiation inhibition regulation of osteoclasts
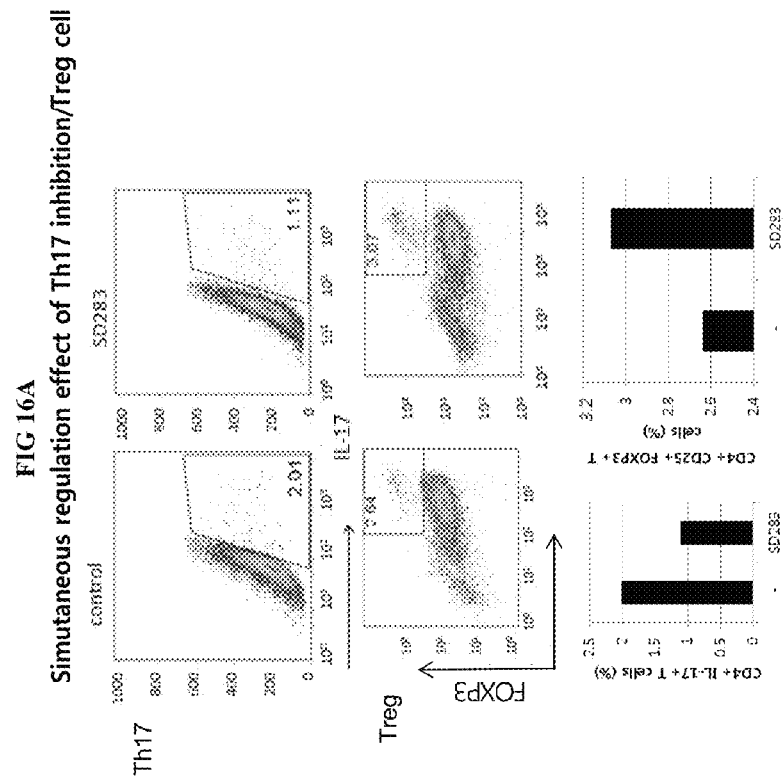
FIG 16A Simutaneous regulation effect of Th17 inhibition/Treg cell
FIG 16C Overactivated-Th17 cell controlling effect
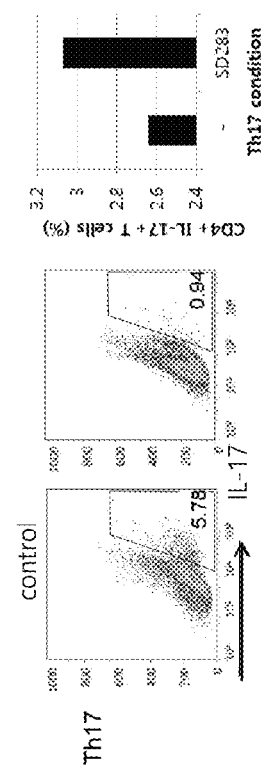

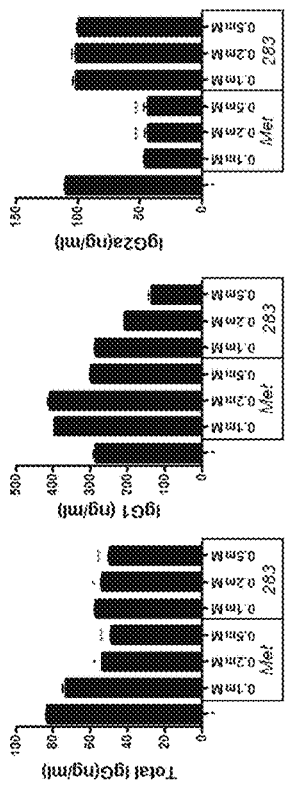
FIG 17A Cytotoxic effect regulation (MTT assay)
FIG 17B Inflammatory cytokine production regulation
FIG 17C Inflammatory cytokine production regulation
FIG 17D Inflammatory gene factor regulation

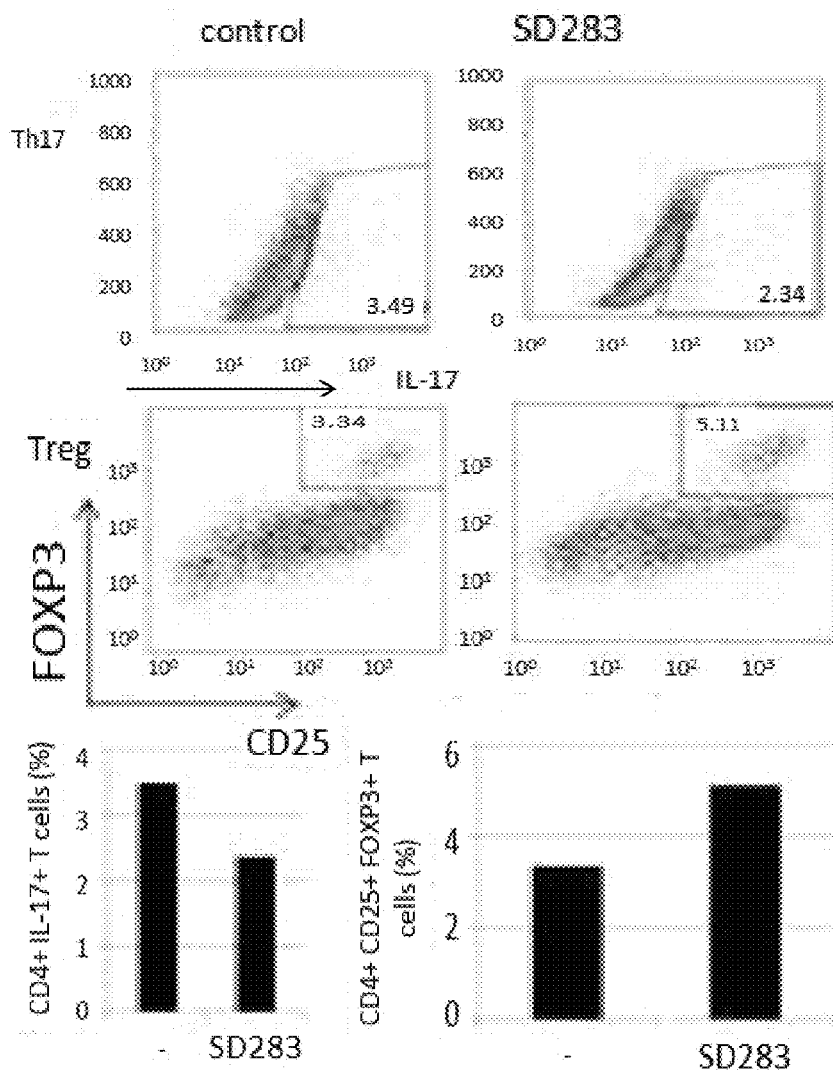

Differentiation inhibition regulation of osteoclasts

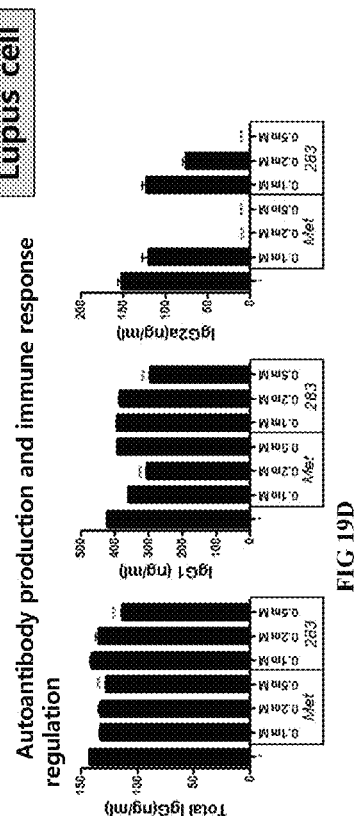
FIG 19A Cytotoxic effect regulation (MTT assay)
FIG 19B Autoantibody production and immune response regulation
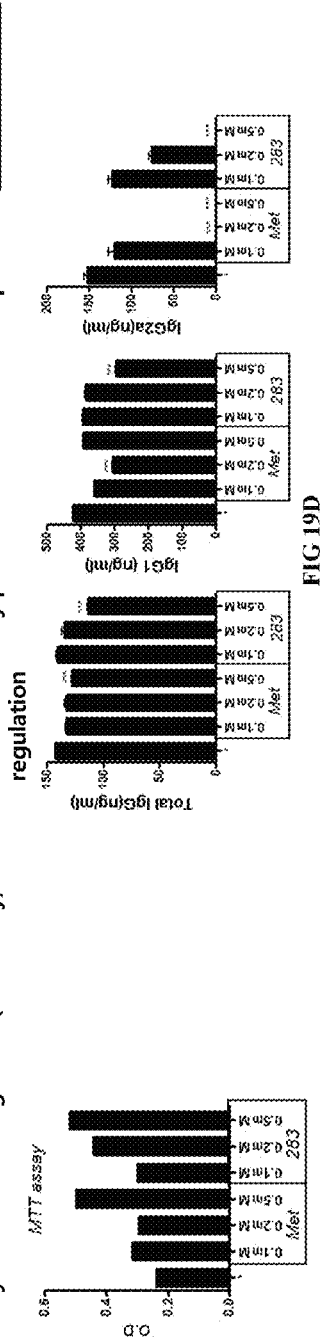
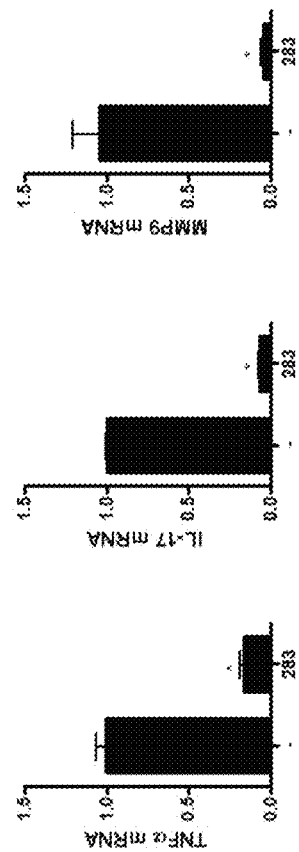
FIG 19C Inflammatory cytokine production regulation
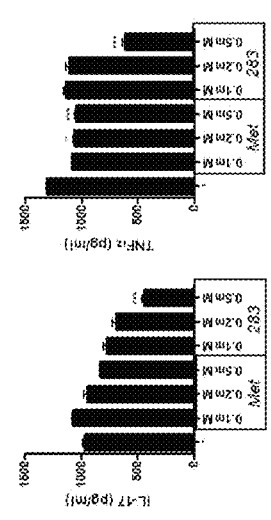
FIG 19D Inflammatory gene factor regulation

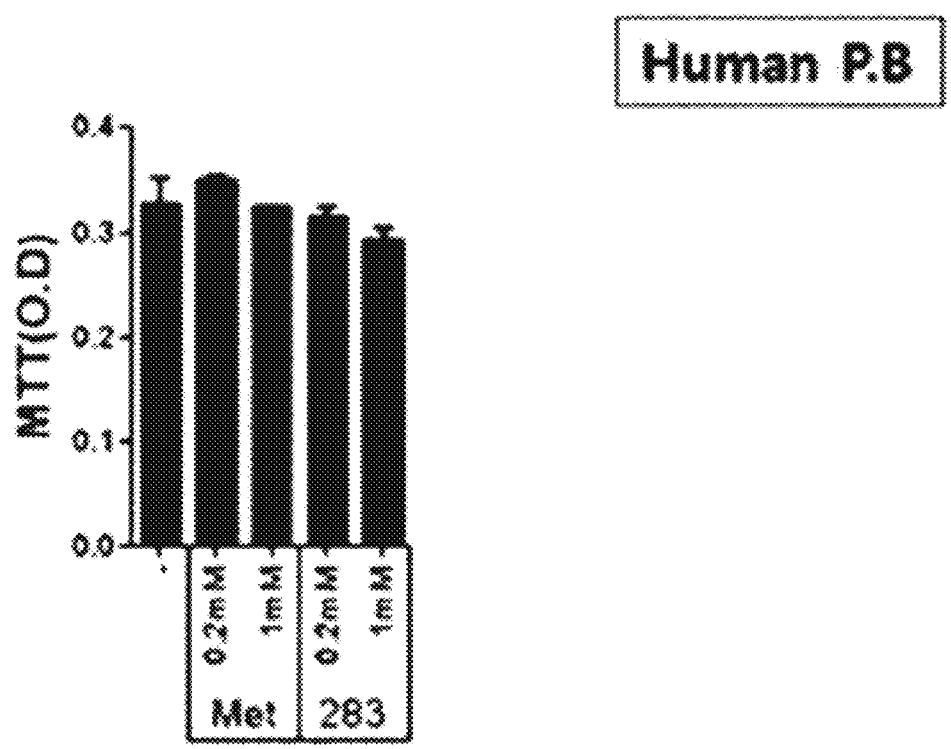

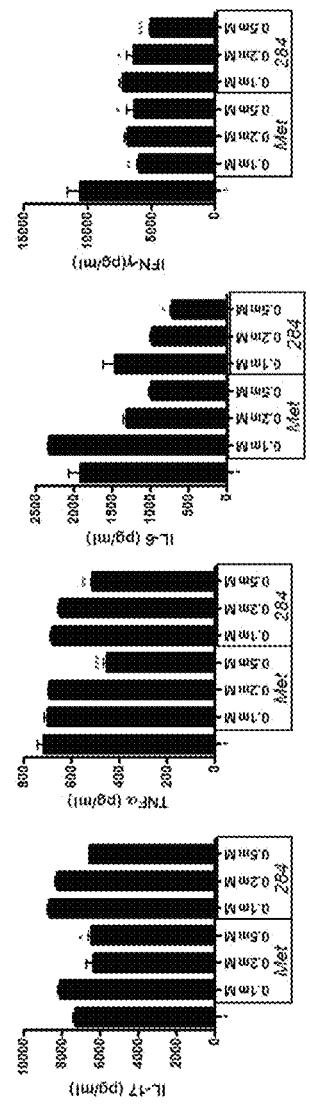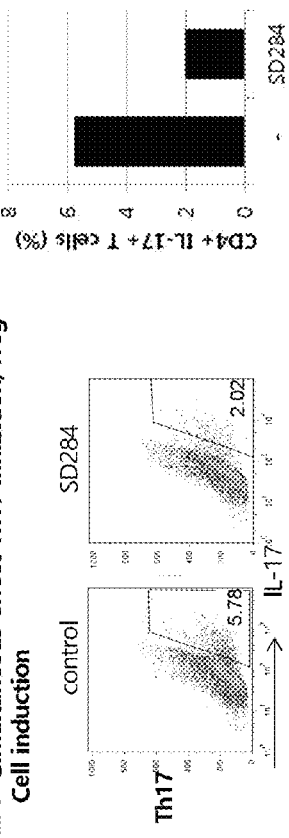
FIG 22A Cytotoxic effect regulation (MTT assay)
FIG 22B Inflammatory cytokine production regulation
FIG 22C Simultaneous effect Th17 inhibition/Treg Cell induction

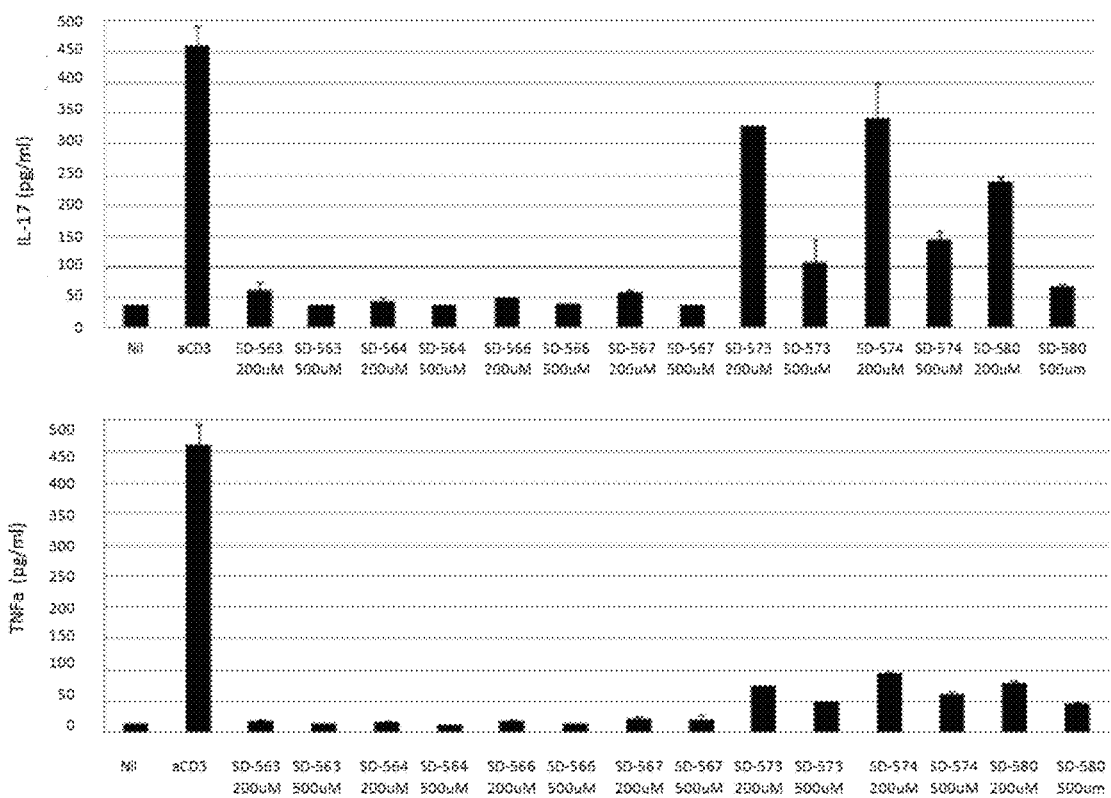

COMPOUND HAVING IMMUNE DISEASE TREATMENT EFFECT AND USE THEREOF

TECHNICAL FIELD

The present invention relates to a novel compound capable of effectively preventing and treating immune diseases and a use thereof.

BACKGROUND ART

An immune disease is a disease mean diseases in which components cause, mediate, or contribute the pathological conditions of the mammals, and particularly, inflammatory disorder is one of the most important health problems around the world. Inflammation is a generally localized protective response of body tissues to the host intrusion by external substances or harmful stimuli. The cause of inflammation may be a state associated with infectious causes such as bacteria, viruses, and parasites; physical causes such as burns or radiation; chemicals such as toxins, drugs, or industrial agents; it may be a condition associated with the immune responses such as allergy and autoimmune responses, or oxidative stress.

The inflammation is characterized by pain, a red phenomenon, swelling, heat, and an eventual functional loss of an infected area. These symptoms are results of a series of complex interactions occurring between cells in the immune system. As a result, due to the response of the cells, an interaction network of inflammatory mediators in many groups is generated: A protein (for example, cytokines, enzymes (e.g., protease, peroxidase), a major basic protein, adhesive molecules (ICAM, VCAM), lipid mediators (e.g., eicosanoid, prostaglandin, leukotriene, platelet activating factor (PAF)), reactive oxygen species (e.g., hydroperoxide, superoxide anion 02-, nitric oxide (NO), etc). However, most of mediators of the inflammation are normal cell activity regulators. Accordingly, while the host is not controlled due to the lack of the inflammatory response, the host is damaged (that is, inflected), and therefore, due to the chronic inflammation, partially, some of the aforementioned mediators are excessively generated and the mediated inflammatory diseases are caused.

Further, an autoimmune disease which is one of the immune diseases has a feature that the immune system causes a spontaneous response by attacking its organ. The responses are caused by recognition of auto-antigen by the T lymphocytes and humoral (production of auto-antigens) and cellular (increase of cytotoxic activity of lymphocytes and macrophages) immune responses are caused. The autoimmune diseases may include diseases below: Rheumatic diseases, psoriasis, systemic dermatomyositis, multiple sclerosis, lupus erythematosus, deterioration of immune responses by antigens, i.e., asthma, drug or food allergies, etc. The diseases are limitative and chronic diseases, and in some cases, fatal, and until now, an effective treating method capable of treating the diseases is not present. Therefore, drugs, medicines, or media capable of reducing or alleviating the diseases in the progress of the corresponding disease may become an important solved means for a patient's health.

Concentrated efforts to find appropriate drugs and methods by searching methods for treating the autoimmune diseases have been made. Today, the treatment of autoimmune diseases is mainly on the basis of the use of immunosuppressive drugs, for example, glucocorticoids, calcineurin inhibitors, and antiproliferatives-antimetabolites. However, such a pharmacological therapy acts on a variety of targets to entirely decrease the immune function. If not, in the case of using the pharmacological therapy for a long time, a variety of cytotoxic actions become the problem to suppress the immune system by a non-specific manner and thus the patients may be exposed to the risk of infections and cancer. Calcineurin and glucocorticoid have another problem due to their nephrotoxicity and diabetes induced characteristics, and thus in the case of some of the clinical symptoms (e.g., renal insufficiency, diabetes, etc.), the use thereof is restricted.

Accordingly, as a substance capable of treating immune diseases such as autoimmune diseases and inflammatory diseases, the development of novel therapeutic agents having an excellent treating effect without side effects is required.

Therefore, the present inventors confirmed that a newly synthesized compound can effectively treat the immune diseases while searching materials having less human side effects and capable of preventing or treating effectively the immune diseases and completed the present invention.

DISCLOSURE

Technical Problem

The present invention is directed to provide a novel compound.

The present invention is also directed to provide a pharmaceutical composition for preventing or treating immune diseases comprising the novel compound as an active ingredient.

Further, the present invention is also directed to provide an immunoregulatory agent comprising the novel compound as an active ingredient.

Further, the present invention is also directed to provide a method of decreasing the differentiation of undifferentiated T cells to Th17 cells and the activity of Th17 cells by treating the novel compound of the present invention in the undifferentiated T cells in vitro.

Further, the present invention is also directed to provide a method of increasing the differentiation of undifferentiated T cells to Treg cells and the activity of Treg cells by treating the novel compound of the present invention in the undifferentiated T cells in vitro.

Technical Solution

One aspect of the present invention provides novel biguanide derivative compounds.

Another aspect of the present invention provides a pharmaceutical composition for preventing or treating immune diseases containing the novel compound of the present invention as an active ingredient.

The compound may decrease or inhibit the production of inflammatory cytokines, inhibit the production of auto-antibodies, and inhibit the differentiation of osteoclasts.

The inflammatory cytokine may be IL-17, IL-6, TNF-α, IFN-γ, MMP-9, or STAT-3.

The antibody may be IgG, IgG1, or IgG2a.

The compound may promote or increase the activity of regulatory T cells and decrease or inhibit the activity of Th17 cells as pathological cells.

The compound may be contained in the composition at a concentration of 0.1 mM to 10 mM.

The immune disease may be selected from the group consisting of autoimmune diseases; inflammatory diseases; and transplantation rejection diseases of cells, tissues or organs.

The immune disease may be selected from rheumatoid arthritis, Behcet's disease, multiple myositis or skin myositis, autoimmune hematocytopenia, autoimmune myocarditis, atopic dermatitis, asthma, primary cirrhosis, dermatomyositis, Goodpasture syndrome, autoimmune meningitis, sjogren's syndrome, lupus, Addison's disease, alopecia areata, ankylosing myelitis, autoimmune hepatitis, autoimmune mumps, Crohn's disease, insulin-dependent diabetes, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, sarcoidosis, scleroderma, spinal arthrosis, thyroiditis, vasculitis, vitiligo, myxedema, pernicious anemia, mitochondrial-related syndromes, and ulcerative colitis.

The transplantation rejection disease may be a graft versus host disease.

Yet another aspect of the present invention provides an immunoregulatory agent containing the novel compound of the present invention as an active ingredient.

Still another aspect of the present invention provides a method of decreasing differentiation to Th17 cells of undifferentiated T cells and activity of the Th17 cells by treating the novel compound of the present invention in the undifferentiated T cells in vitro.

Still yet another aspect of the present invention provides a method of increasing differentiation to Treg cells of undifferentiated T cells and activity of the Treg cells by treating the novel compound of the present invention in the undifferentiated T cells in vitro.

Advantageous Effects

The present invention relates to a novel compound capable of effectively preventing and treating immune diseases and a use thereof. The novel compound of the present invention has effects of inhibiting the production of inflammatory cytokines, increasing the activity of regulatory T cells having immune regulatory functions, inhibiting the production of auto-antibodies to regulate excessive immune responses, and inhibiting the differentiation of osteoclasts, and thus can be used for treating immune diseases, such as autoimmune disease, inflammatory disease, and transplant rejection diseases, which are caused by abnormal regulation of various kinds of immune responses.

DESCRIPTION OF DRAWINGS

The patent or application file contains at least one drawing executed in color. Copies of this patent or patent application publication with color drawing(s) will be provided by the Office upon request and payment of the necessary fee.

FIG. 6 illustrates a result of analyzing Th17 inhibition and promotion of Treg activity according to treatment of a SD-281 compound for each concentration by targeting spleen cells of a mouse in which lupus is caused.

FIG. 8 illustrates a result of analyzing cytotoxicity, autoantibody production, inflammatory cytokine production, and inflammatory gene expression according to treatment of a SD-282 compound for each concentration by targeting spleen cells of a normal mouse.

FIG. 10 illustrates a result of analyzing cytotoxicity, autoantibody production, inflammatory cytokine production, and inflammatory gene expression according to treatment of a SD-282 compound for each concentration by targeting spleen cells of a mouse in which rheumatoid arthritis is induced.

FIG. 12 illustrates a result of analyzing cytotoxicity, autoantibody production, inflammatory cytokine production, and inflammatory gene expression according to treatment of a SD-282 compound for each concentration by targeting spleen cells of a mouse in which lupus is caused.

FIG. 14 illustrates a result of analyzing cytotoxicity and inflammatory cytokine production according to treatment of a SD-282 compound for each concentration by targeting lymphocytes isolated from human peripheral blood.

FIG. 15 illustrates a result of analyzing cytotoxicity, autoantibody production, inflammatory cytokine production, and inflammatory gene expression according to treatment of a SD-283 compound for each concentration by targeting spleen cells of a normal mouse.

FIG. 16 illustrates a result of analyzing Th17 inhibition, promotion of Treg activity, and differentiation inhibition of osteoclasts, and inhibition of hyperactivated Th17 according to treatment of a SD-283 compound for each concentration by targeting spleen cells of a normal mouse.

FIG. 17 illustrates a result of analyzing cytotoxicity, autoantibody production, inflammatory cytokine production, and inflammatory gene expression according to treatment of a SD-283 compound for each concentration by targeting spleen cells of a mouse in which rheumatoid arthritis is induced.

FIG. 19 illustrates a result of analyzing cytotoxicity, autoantibody production, inflammatory cytokine production, and inflammatory gene expression according to treatment of a SD-283 compound for each concentration by targeting spleen cells of a mouse in which lupus is caused.

FIG. 22 illustrates a result of analyzing cytotoxicity, inflammatory cytokine production, Th17 inhibition, and promotion of Treg activity according to treatment of a SD-284 compound for each concentration by targeting spleen cells of a normal mouse.

FIG. 24 illustrates a result of analyzing production inhibition activity of TNF-α and IL-17 which are inflammatory cytokines of novel compounds of the present invention.

MODES OF THE INVENTION

Figure 1A:
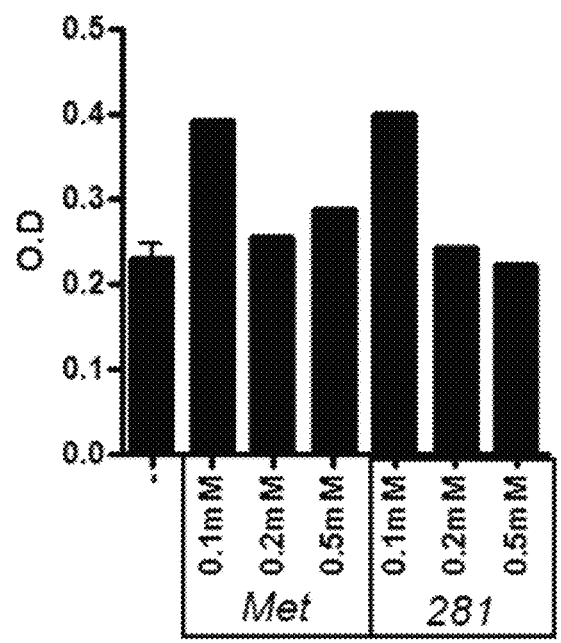
FIG. 1 illustrates a result of analyzing cytotoxicity, autoantibody production, inflammatory cytokine production, and inflammatory gene expression according to treatment of a SD-281 compound for each concentration by targeting spleen cells of a normal mouse. In this case, it is observed that the differentiation of osteoclasts is regulated according to the treatment of the SD-281 compound.
Figure 1B:
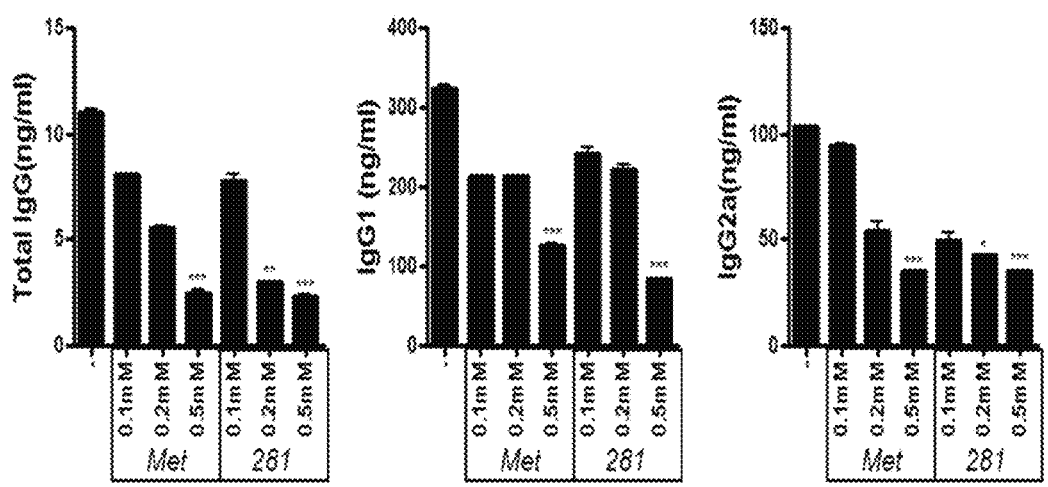
Figure 1C:
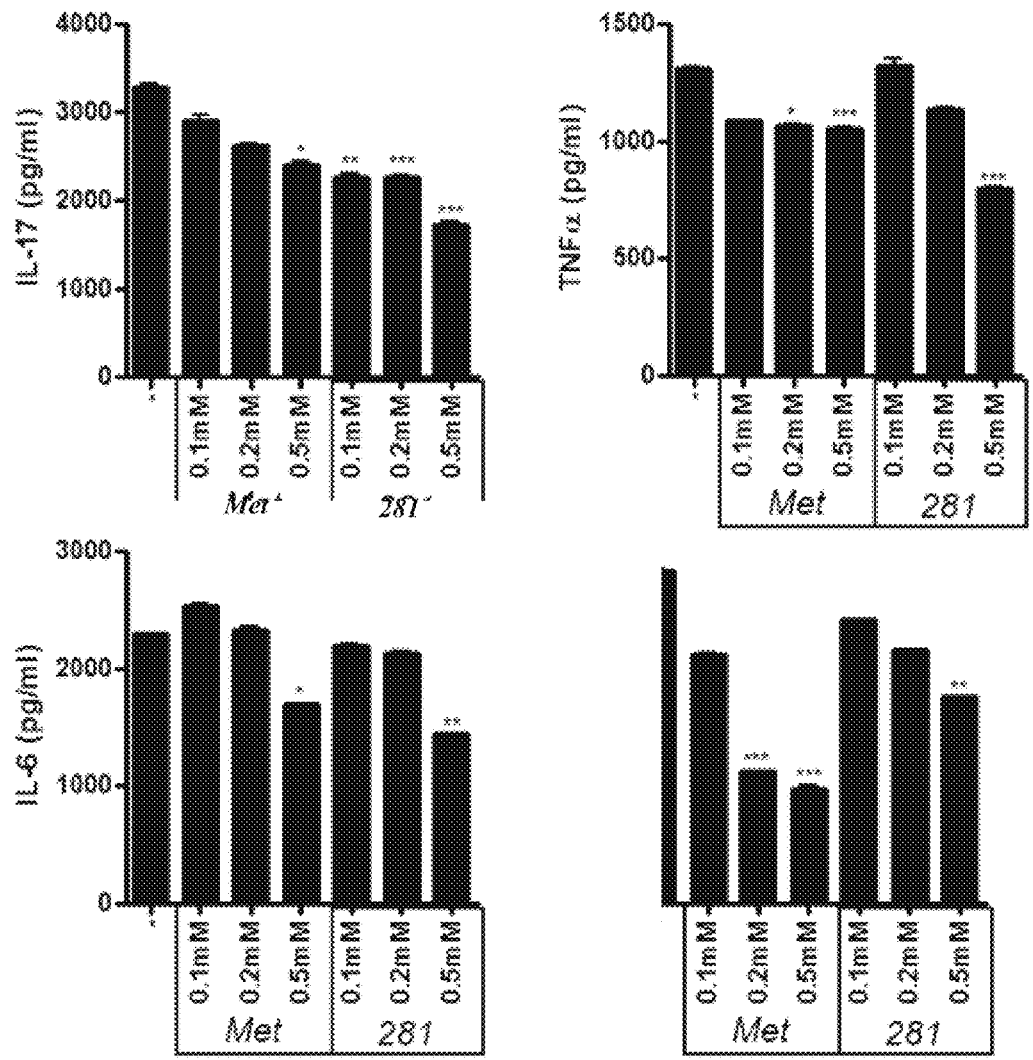
Figure 1D:
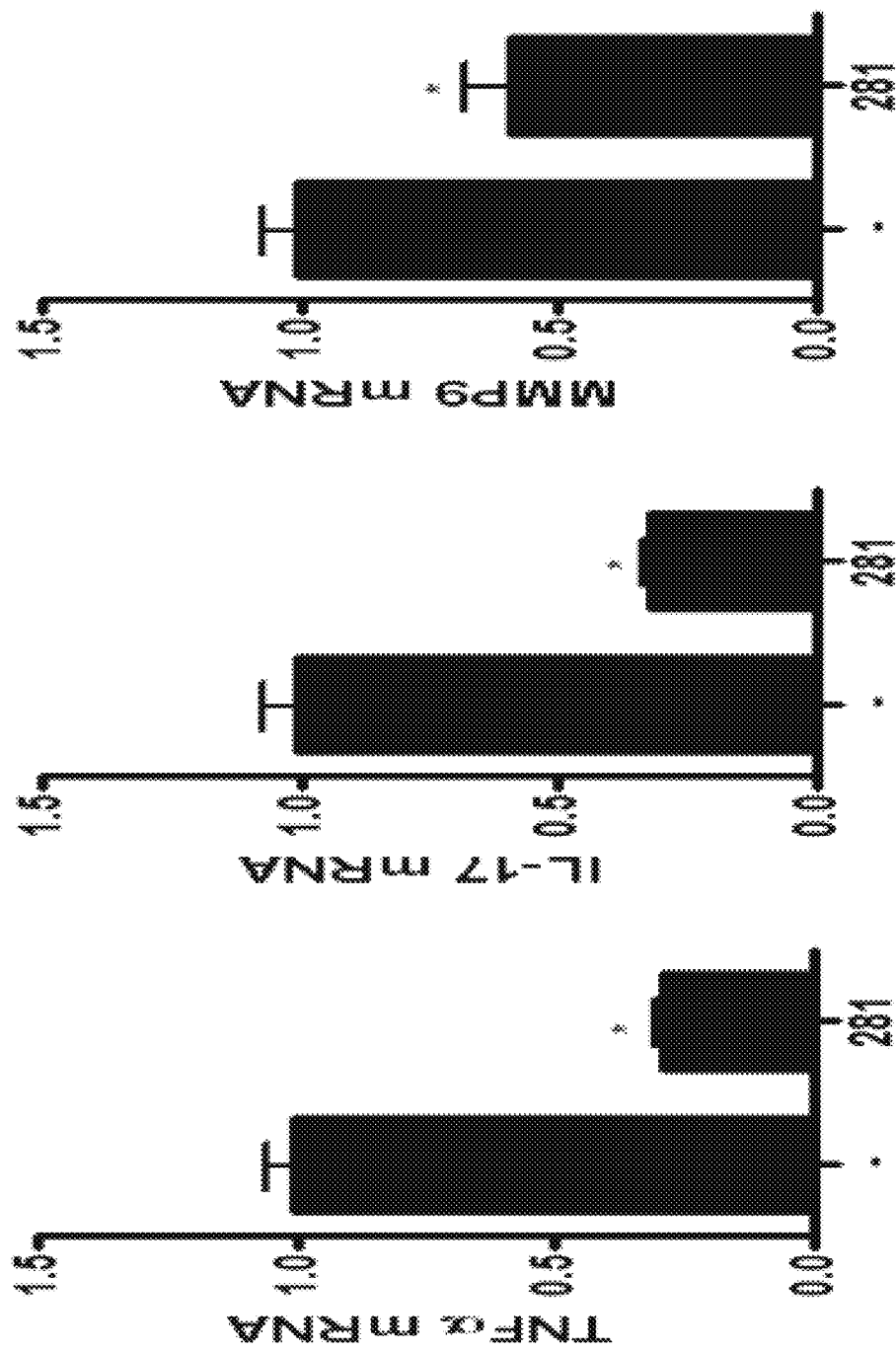
Figure 2A:
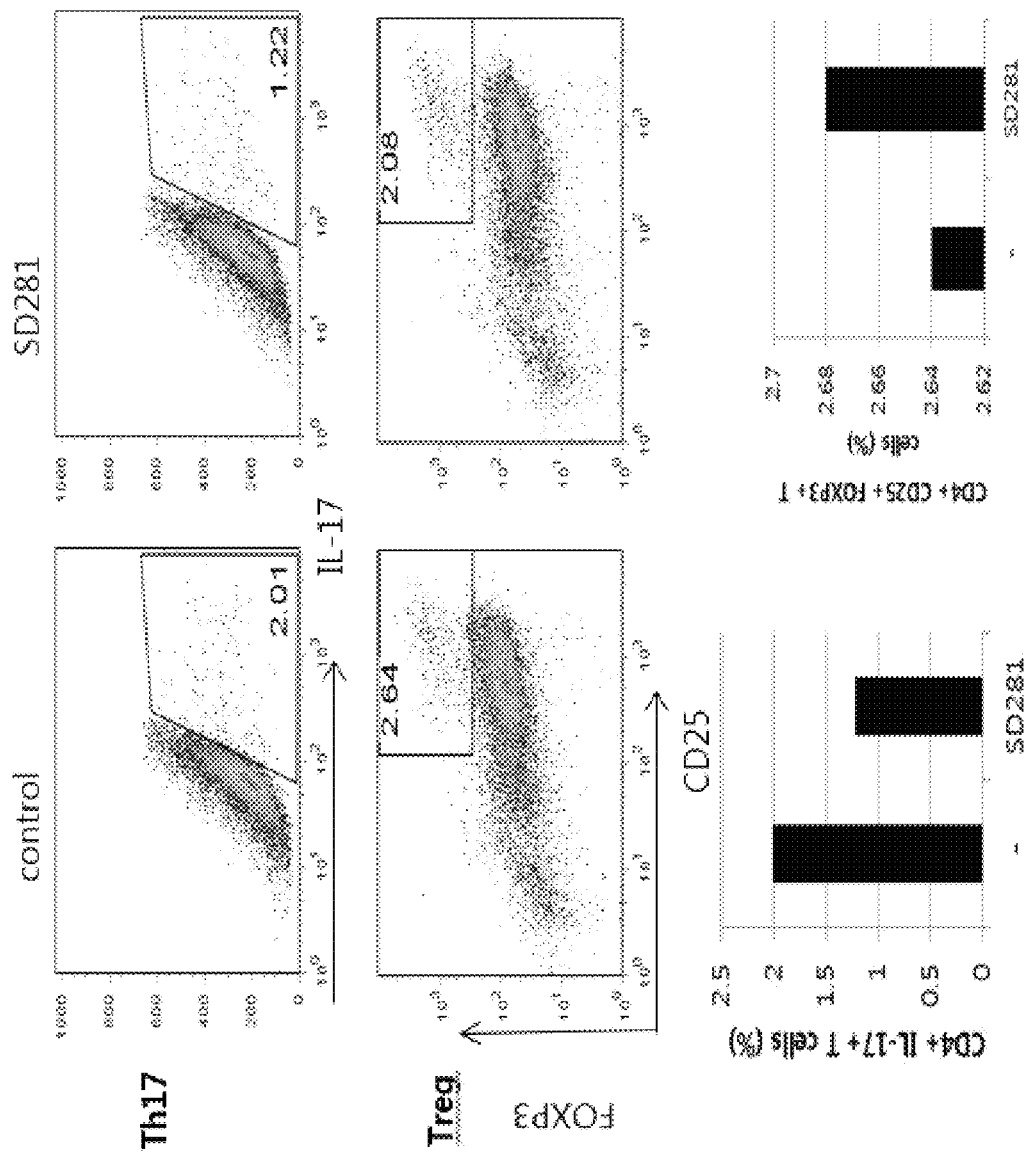
FIG. 2 illustrates a result of analyzing Th17 inhibition, promotion of Treg activity, and inhibition of hyperactivated Th17 and a result of analyzing differentiation inhibition of osteoclasts induced from bone marrow cells (BM) of a mouse according to the treatment of the SD-281 compound for each concentration by targeting spleen cells of a normal mouse.
Figure 2B:
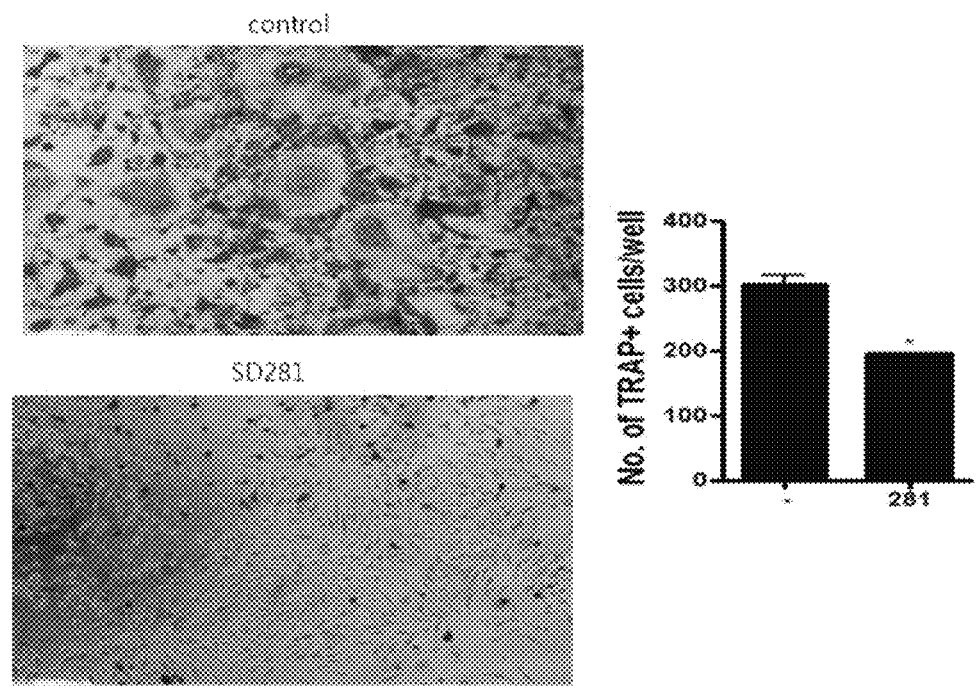
Figure 2C:
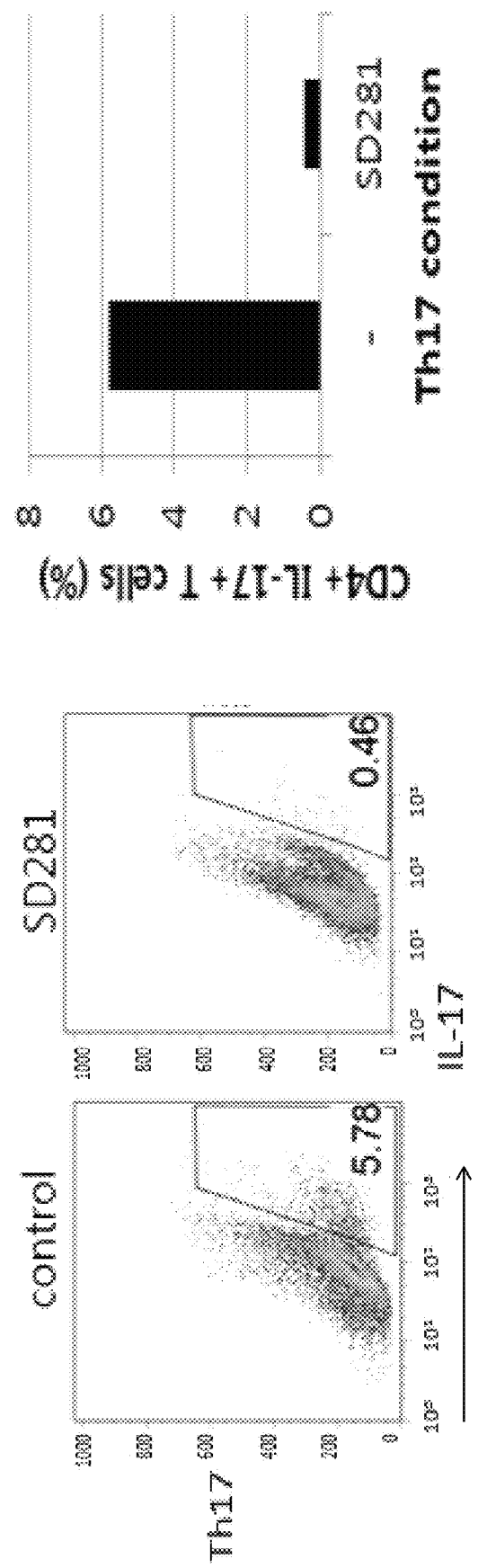
Figure 3A:
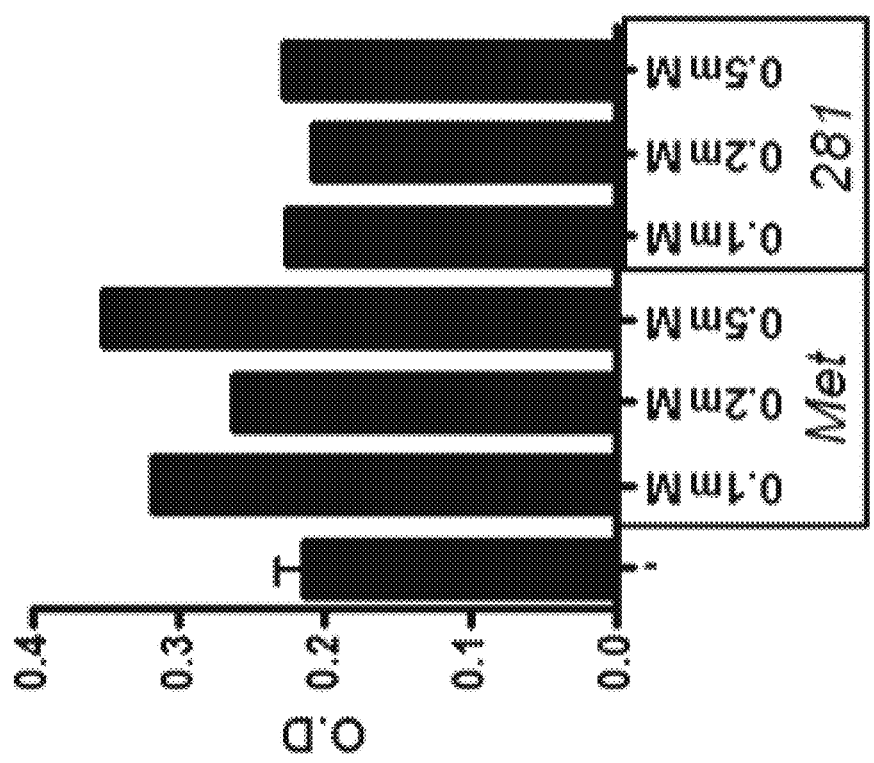
FIG. 3 illustrates a result of analyzing cytotoxicity, autoantibody production, inflammatory cytokine production, and inflammatory gene expression according to treatment of a SD-281 compound for each concentration by targeting spleen cells of a mouse in which rheumatoid arthritis is induced.
Figure 3B:
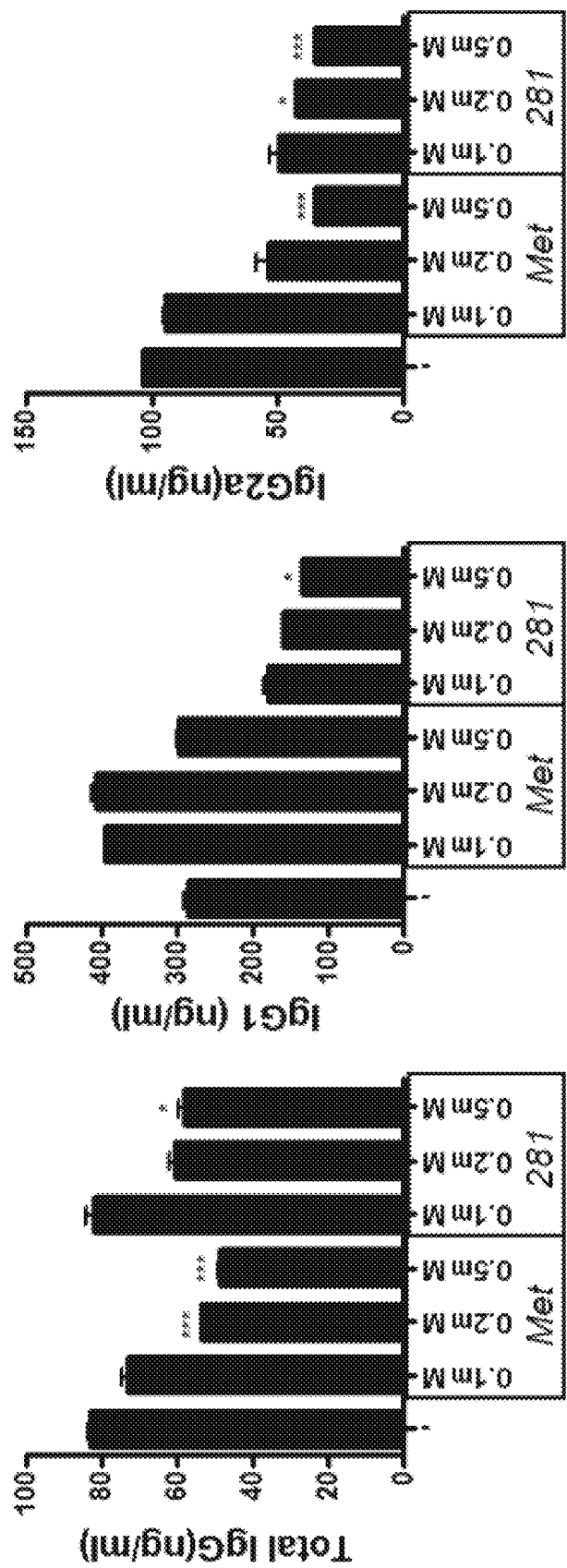
Figure 4A:
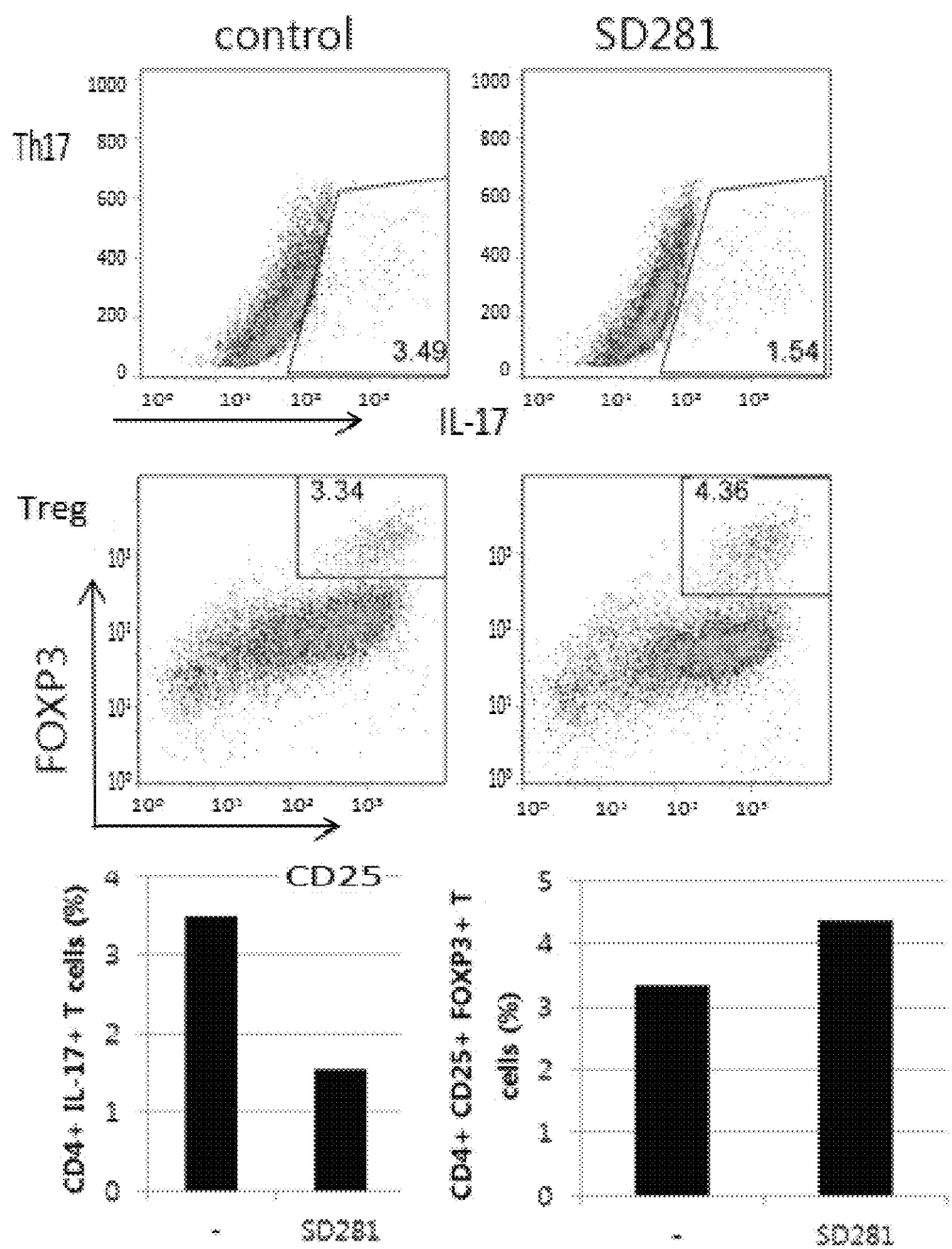
FIG. 4 illustrates a result of analyzing Th17 inhibition, promotion of Treg activity, and differentiation inhibition of osteoclasts according to treatment of a SD-281 compound for each concentration by targeting spleen cells of a mouse in which rheumatoid arthritis is induced.
Figure 5A:
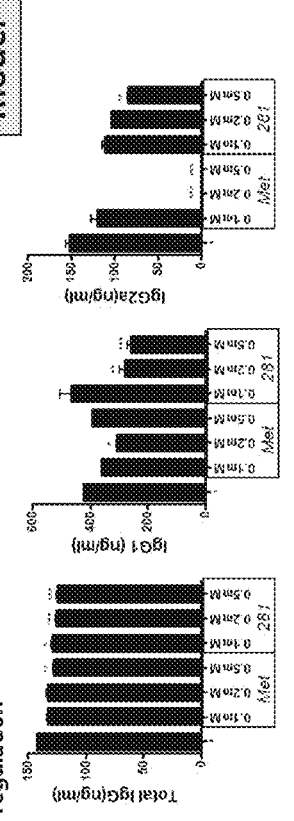
FIG. 5 illustrates a result of analyzing cytotoxicity, autoantibody production, inflammatory cytokine production, and inflammatory gene expression according to treatment of a SD-281 compound for each concentration by targeting spleen cells of a mouse in which lupus is caused.
Figure 5C:
Figure 5B:
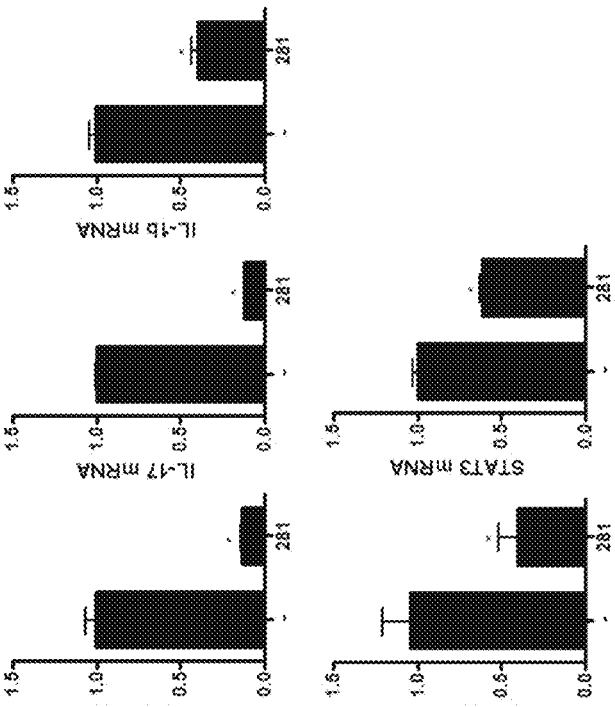
Figure 5D:
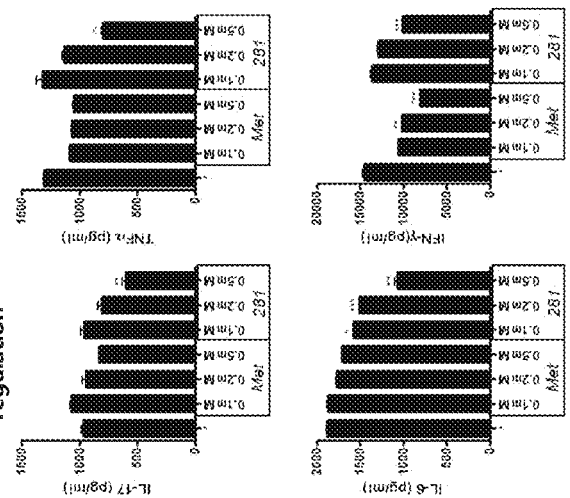
Figure 7B:
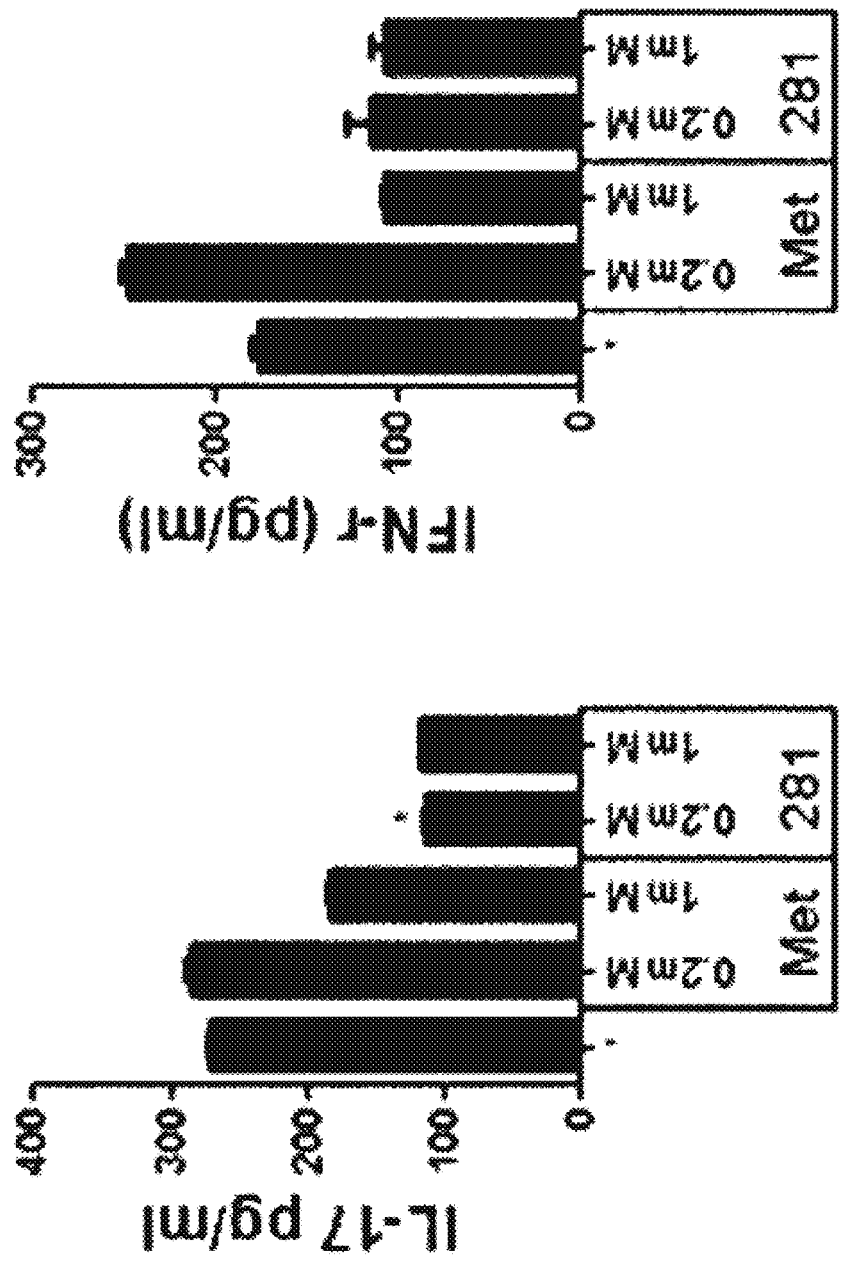
FIG. 7 illustrates a result of analyzing cytotoxicity and inflammatory cytokine production according to treatment of a SD-281 compound for each concentration by targeting lymphocytes isolated from human peripheral blood.
Figure 9A:
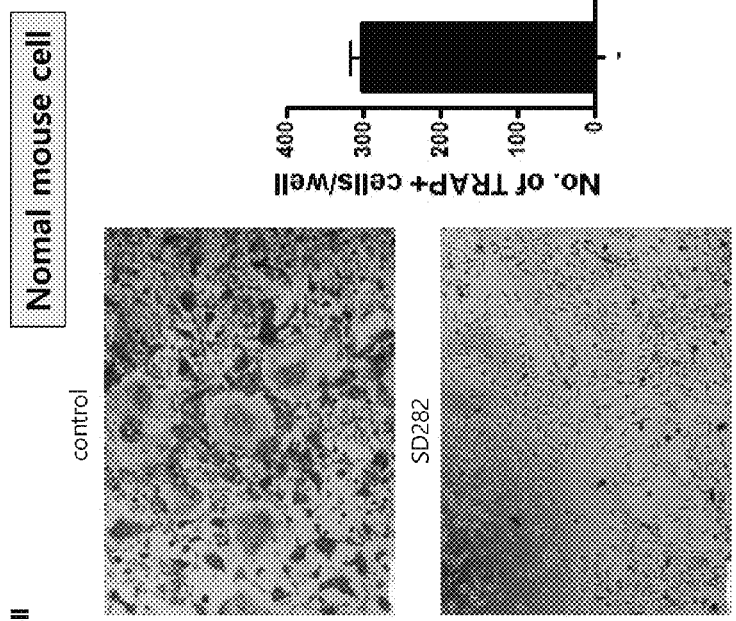
FIG. 9 illustrates a result of analyzing Th17 inhibition, promotion of Treg activity, and differentiation inhibition of osteoclasts, and inhibition of hyperactivated Th17 according to treatment of a SD-282 compound for each concentration by targeting spleen cells of a normal mouse.
Figure 9B:
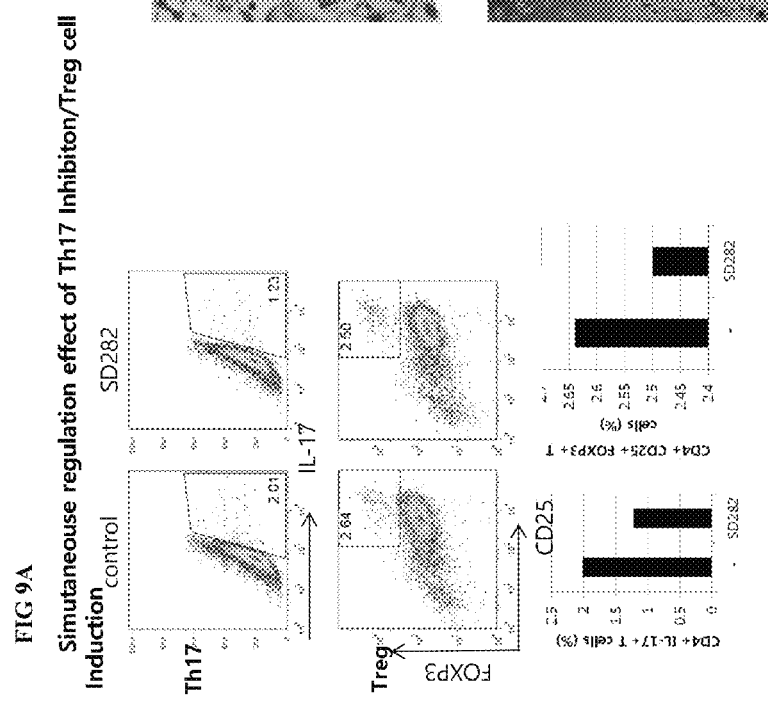
Figure 9C:
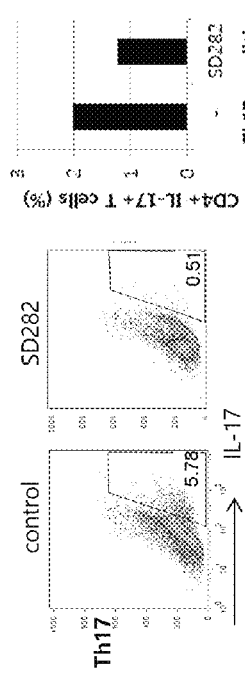
Figure 11B:
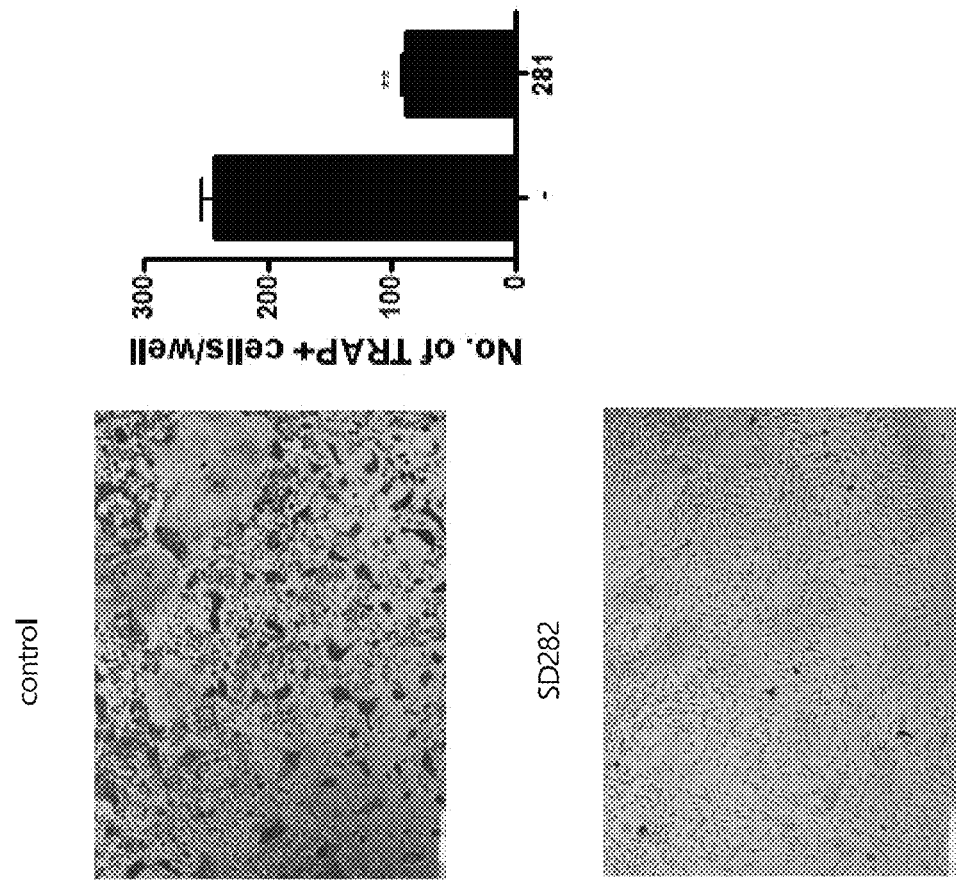
FIG. 11 illustrates a result of analyzing Th17 inhibition, promotion of Treg activity, and differentiation inhibition of osteoclasts according to treatment of a SD-282 compound for each concentration by targeting spleen cells of a mouse in which rheumatoid arthritis is induced.
Figure 11A:
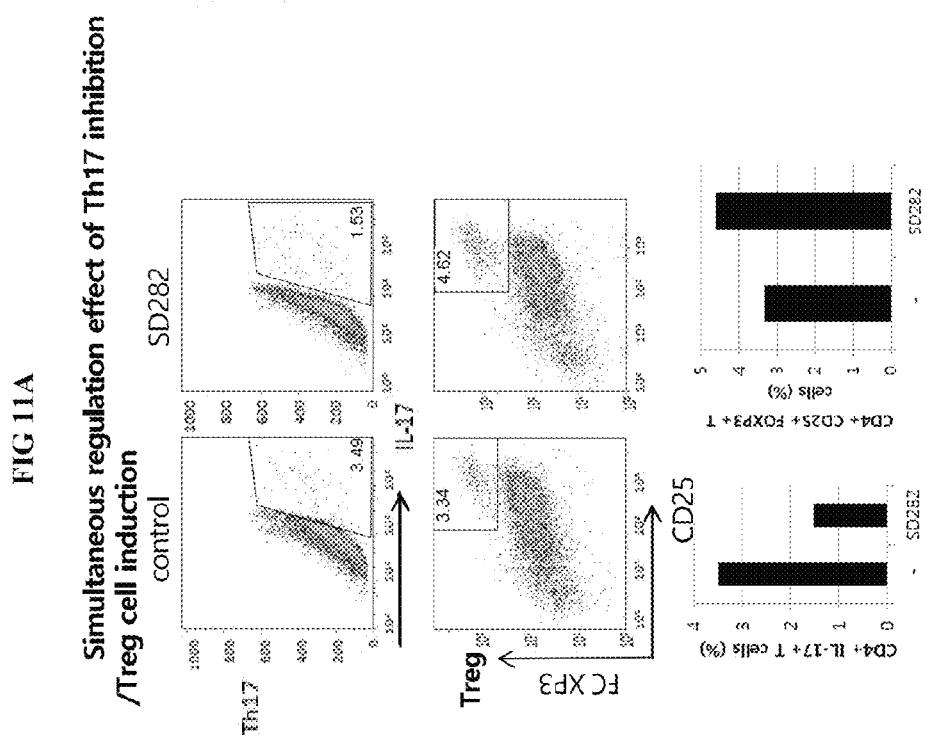
Figure 13:
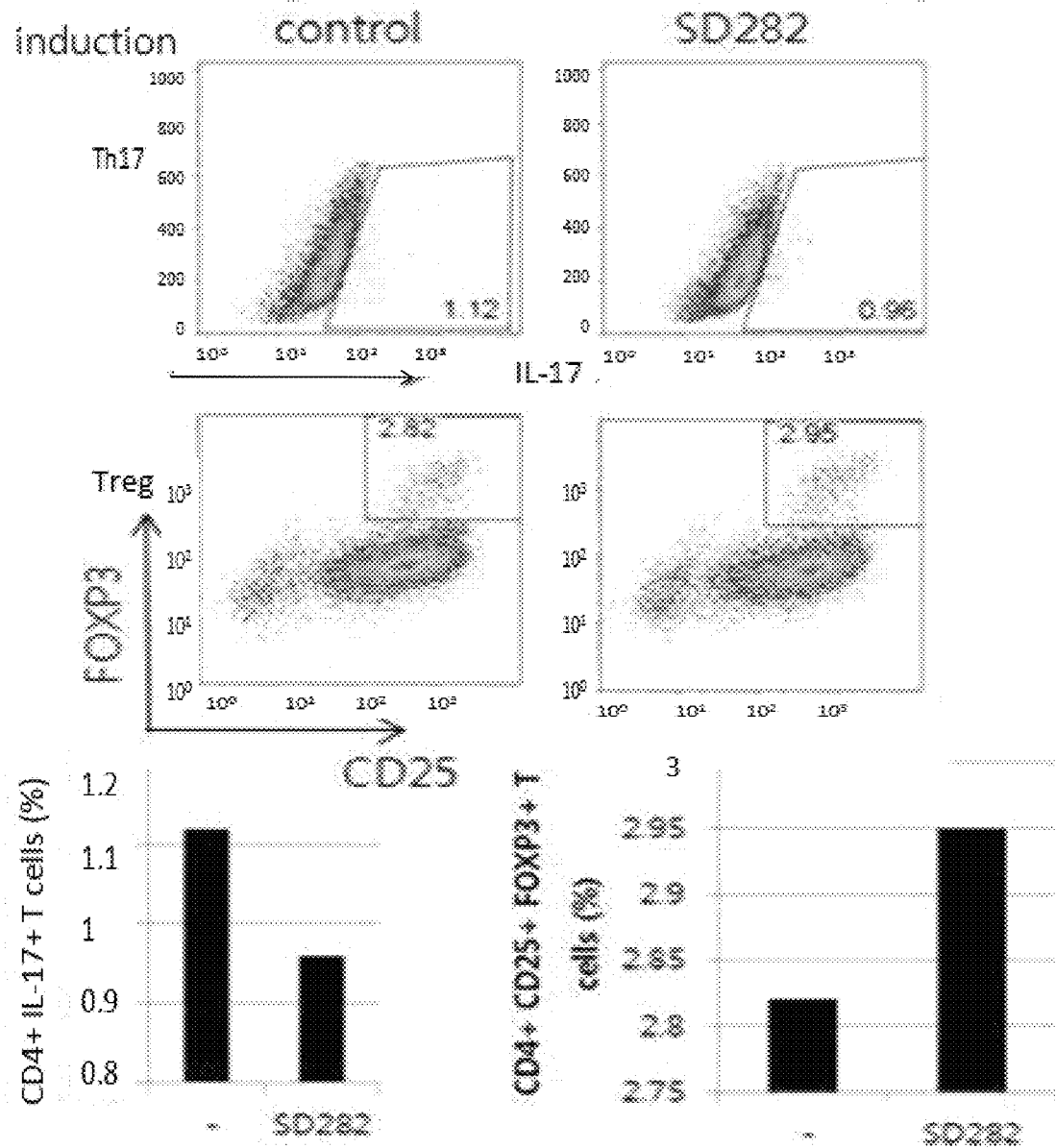
FIG. 13 illustrates a result of analyzing Th17 inhibition and promotion of Treg activity according to treatment of a SD-282 compound for each concentration by targeting spleen cells of a mouse in which lupus is caused.
Figure 18B:
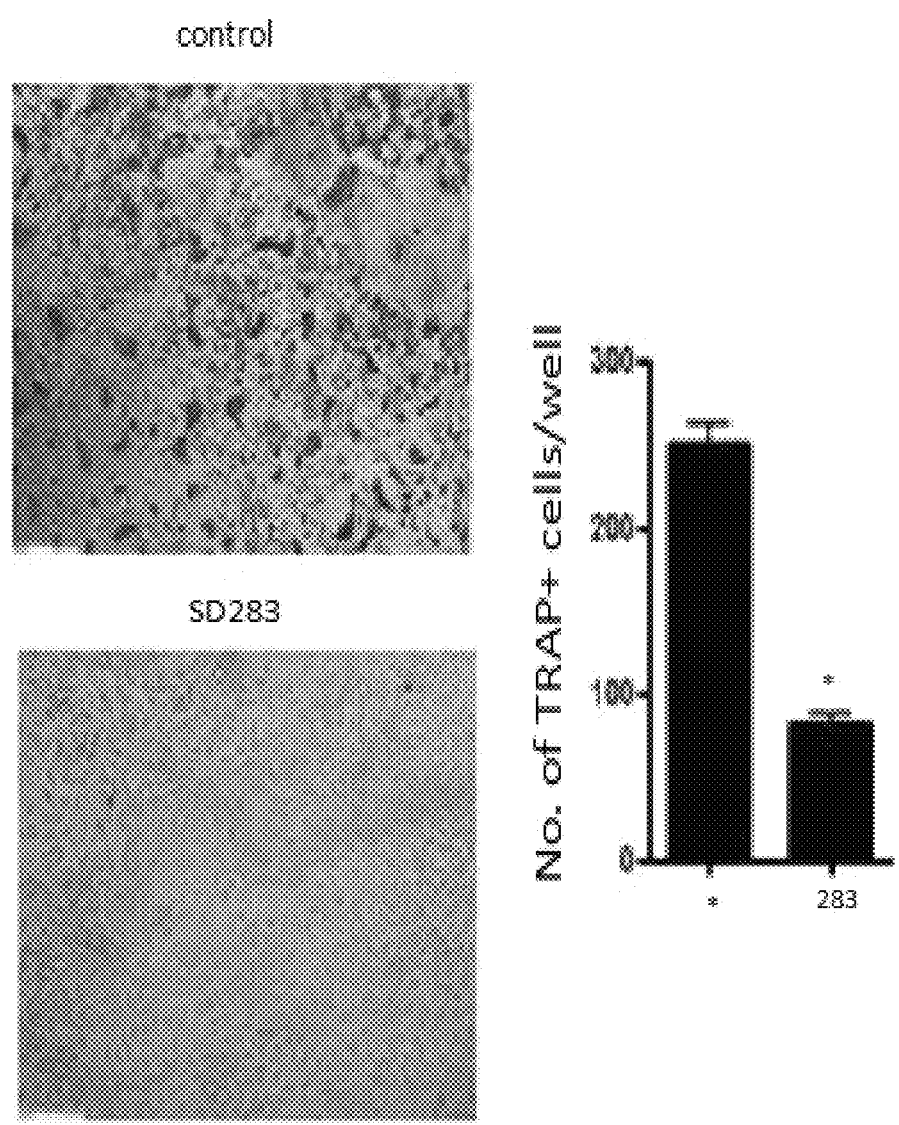
FIG. 18 illustrates a result of analyzing Th17 inhibition, promotion of Treg activity, and differentiation inhibition of osteoclasts according to treatment of a SD-283 compound for each concentration by targeting spleen cells of a mouse in which rheumatoid arthritis is induced.
Figure 20:
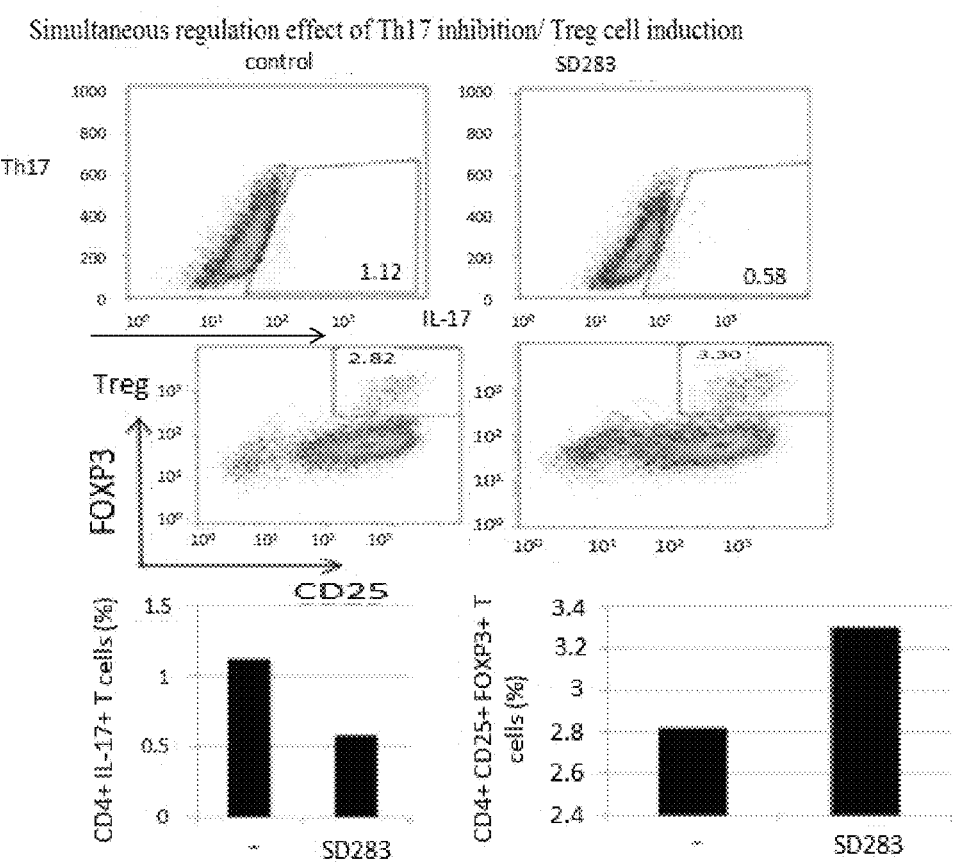
FIG. 20 illustrates a result of analyzing Th17 inhibition and promotion of Treg activity according to treatment of a SD-283 compound for each concentration by targeting spleen cells of a mouse in which lupus is caused.
Figure 21B:
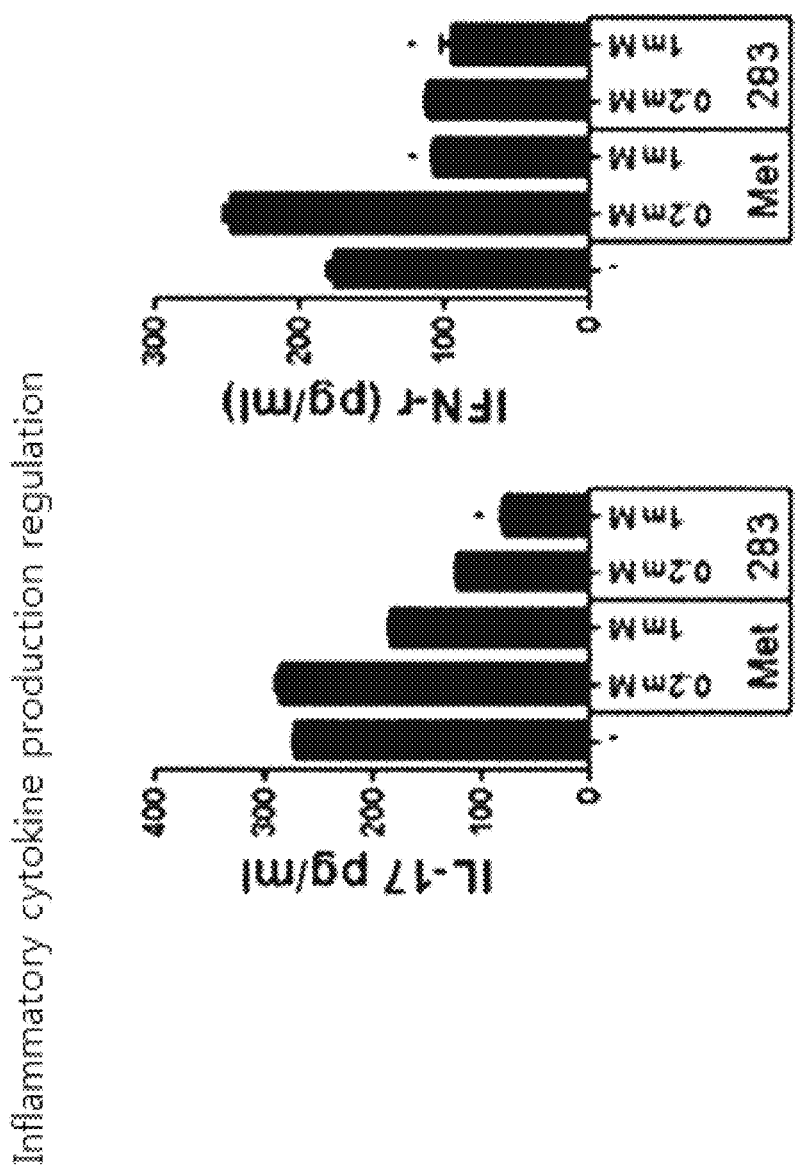
FIG. 21 illustrates a result of analyzing cytotoxicity and inflammatory cytokine production according to treatment of a SD-283 compound for each concentration by targeting lymphocytes isolated from human peripheral blood.
Figure 23A:
FIG. 23 illustrates a result of analyzing cytotoxicity and inflammatory cytokine production according to treatment of a SD-284 compound for each concentration by targeting lymphocytes isolated from human peripheral blood.
Figure 23B:
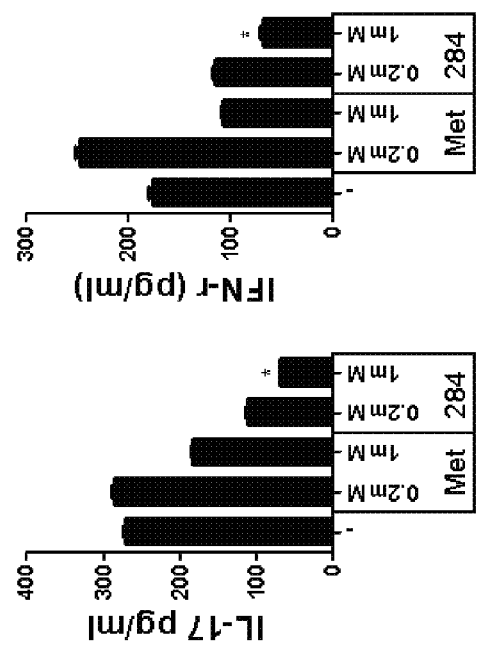

The present invention has a feature that it is first identified that novel compounds below can be used as a novel therapeutic agent capable of effectively preventing or treating immune diseases.

Accordingly, the present invention may provide a novel compound represented by the following Chemical Formula or a pharmaceutically acceptable salt thereof.

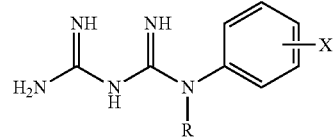

In Chemical Formula, X is at least one of F, Cl, Br, or H; and R is hydrogen or alkyl.

More preferably, the compound in Chemical Formula may be any one selected from 24 compounds disclosed in the following Table.

| NO. | Compound Code | Compound Name | Compound Structure |
|---|---|---|---|
| 1 | SD-281 | N-(3,4-Difluorophenyl)-N-ethylbiguanide | 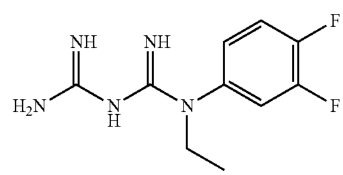 [SMILES: CCN(C(=N)NC(=N)N)c1ccc(F)c(F)c1] |
| 2 | SD-282 | N-Ethyl-N-(4-fluorophenyl)biguanide | 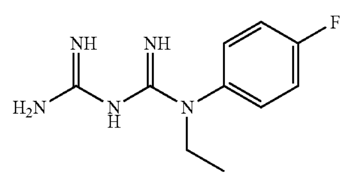 [SMILES: CCN(C(=N)NC(=N)N)c1ccc(F)cc1] |
| 3 | SD-283 | N-(2,4-Difluorophenyl)-N-ethylbiguanide | 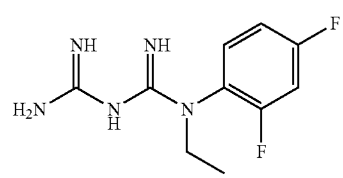 [SMILES: CCN(C(=N)NC(=N)N)c1ccc(F)cc1F] |
| 4 | SD-284 | N-(2,4-Difluorophenyl)-N-methylbiguanide | 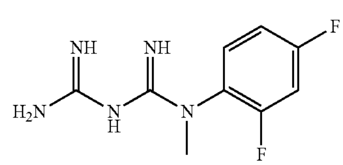 [SMILES: CN(C(=N)NC(=N)N)c1ccc(F)cc1F] |

-continued

| NO. | Compound Code | Compound Name | Compound Structure |
|---|---|---|---|
| 5 | SD-562 | N-(4-Chorophenyl)biguanide | 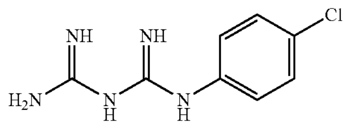 [SMILES: N=C(N)NC(=N)Nc1ccc(Cl)cc1] |
| 6 | SD-563 | N-(4-Bromophenyl)biguanide | 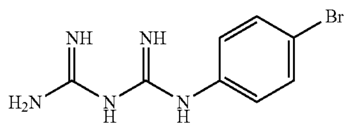 [SMILES: N=C(N)NC(=N)Nc1ccc(Br)cc1] |
| 7 | SD-564 | N-(3-Chlorophenyl)biguanide | 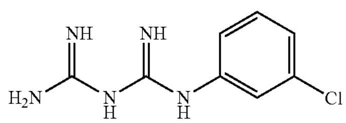 |
| 8 | SD-565 | N-(3-Bromophenyl)biguanide | 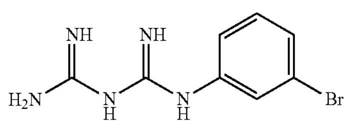 [SMILES: N=C(N)NC(=N)Nc1cccc(Br)c1] |
| 9 | SD-566 | N-(4-Chlorophenyl)-N-ethyl-biguanide | 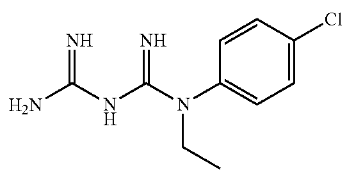 [SMILES: CCN(C(=N)NC(=N)N)c1ccc(Cl)cc1] |
| 10 | SD-567 | N-(4-Bromophenyl)-N-ethyl-biguanide | 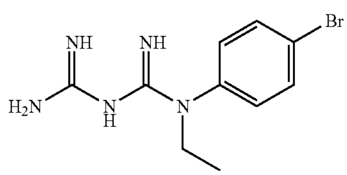 [SMILES: CCN(C(=N)NC(=N)N)c1ccc(Br)cc1] |
| 11 | SD-568 | N-(3-Chlorophenyl)-N-ethyl-biguanide | 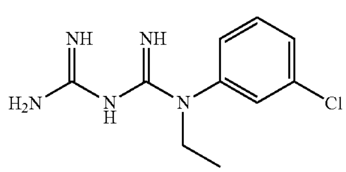 |
| 12 | SD-569 | N-(3-Bromophenyl)-N-ethyl-biguanide | 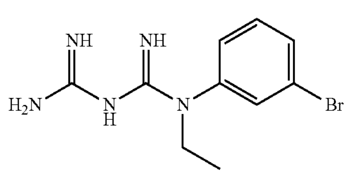 [SMILES: CCN(C(=N)NC(=N)N)c1cccc(Br)c1] |
| 13 | SD-570 | N-Phenylbiguanide | 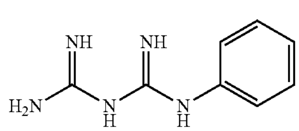 [SMILES: N=C(N)NC(=N)Nc1ccccc1] |
| 14 | SD-571 | N-(3,5-Difluorophenyl)biguanide | 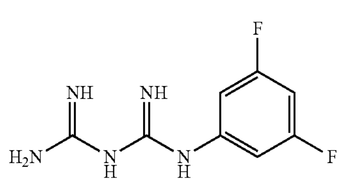 [SMILES: N=C(N)NC(=N)Nc1cc(F)cc(F)c1] |

-continued

| NO. | Compound Code | Compound Name | Compound Structure |
|---|---|---|---|
| 15 | SD-572 | N-(3,4-Difluorophenyl)biguanide | 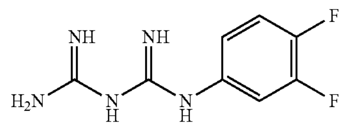 [SMILES: N=C(N)NC(=N)Nc1ccc(F)c(F)c1] |
| 16 | SD-573 | N-Ethyl-N-phenyl biguanide | 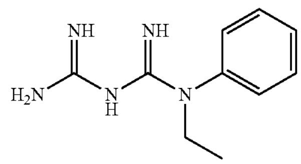 |
| 17 | SD-574 | N-Ethyl-N-(2-fluorophenyl)biguanide | 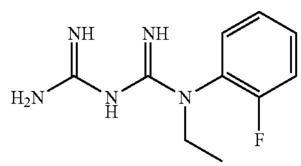 [SMILES: CCN(C(=N)NC(=N)N)c1ccccc1F] |
| 18 | SD-575 | N-Ethyl-N-(3-fluorophenyl)biguanide | 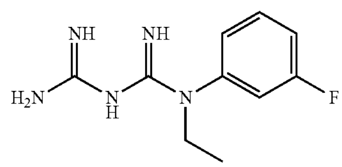 [SMILES: CCN(C(=N)NC(=N)N)c1cccc(F)c1] |
| 19 | SD-576 | N-(3,5-Difluorophenyl)-N-ethylbiguanide | 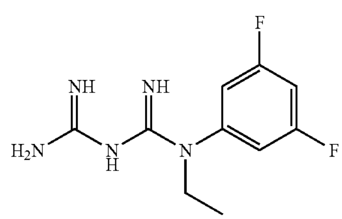 [SMILES: CCN(C(=N)NC(=N)N)c1cc(F)cc(F)c1] |
| 20 | SD-577 | N-(2,5-Difluorophenyl)-N-ethylbiguanide | 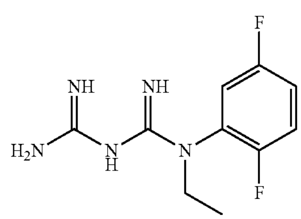 [SMILES: CCN(C(=N)NC(=N)N)c1cc(F)ccc1F] |
| 21 | SD-578 | N-Ethyl-N-(2,3,4-trifluorophenyl)biguanide | 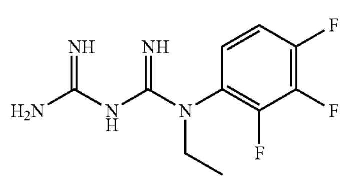 [SMILES: CCN(C(=N)NC(=N)N)c1ccc(F)c(F)c1F] |
| 22 | SD-579 | N-Phenyl-N-isopropyl-biguanide | 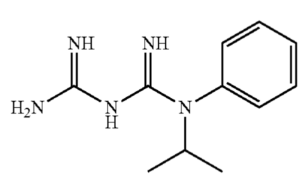 [SMILES: CC(C)N(C(=N)NC(=N)N)c1ccccc1] |

-continued

| NO. | Compound Code | Compound Name | Compound Structure |
|---|---|---|---|
| 23 | SD-580 | N-(2,4-Difluorophenyl)-N-propylbiguanide | 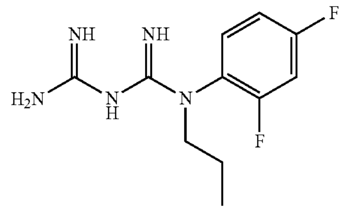 [SMILES: CCCN(C(=N)NC(=N)N)c1ccc(F)cc1F] |
| 24 | SD-581 | N-(4-Difluorophenyl)-N-propylbiguanide | 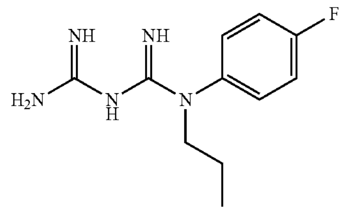 [SMILES: CCCN(C(=N)NC(=N)N)c1ccc(F)cc1] |

The inventors performs an experiment for verifying whether novel compounds synthesized in the present invention can treat the immune diseases, and according to the exemplary embodiment of the present invention, it can be seen that all of the compounds decreases or inhibits the production of inflammatory cytokines, inhibits the production of auto-antibodies, and inhibits the differentiation of osteoclasts. In this case, the inflammatory cytokines are not limited thereto, but may be IL-17, IL-6, TNF-α, IFN-γ, MMP-9, or STAT-3.

Further, in the present invention, it could be seen that the compounds had regulatory ability of inhibiting excessive immune response by inhibiting the production of IgG, IgG1, or IgG2a which was an autoantibody.

Further, the compounds of the present invention promote or increase the activity of regulatory T cells and the activity of Th17 cells as pathological cells is decreased or inhibited.

Accordingly, the inventors may verify a possibility of the compounds which are newly synthesized in the present invention as a novel therapeutic agent capable of effectively treating the immune diseases.

Meanwhile, as a biodefense system for various pathogens, one of cell groups which play a central role in the immune system is T cells. The T cells are produced in the human thymus and differentiated to T cells having a unique characteristic through a series of differentiation processes, and the differentiated T cells are largely divided into Type 1 helper cells Th1 and Type 2 helper cells Th2 according to the function thereof. Among them, as main functions, the Th1 cells are involved in cell-mediated immunity and the Th2 cells are involved in humoral immunity, and two cell groups in the immune system maintains the balance of the immune system through mutual control so as not to be hyperactivated.

Accordingly, most of immune diseases may be caused by unbalance between the two immune cells. For example, it has been known that when the activity of the Th1 cells is abnormally increased, autoimmune diseases may occur, and when the activity of the Th2 cells is abnormally increased, immune diseases caused by hypersensitivity occur.

Meanwhile, according to a recent research result for the differentiation of the Th1 cells, the presence of the immunoregulatory T (Treg) cells as a novel group capable of regulating the activity of the Th1 cells becomes known and thus researches for the treatment of the immune diseases using the Treg cells have emerged. The Treg cells have a characteristic of inhibiting the function of the abnormally activated immune cells to control inflammatory response and thus a lot of experiments of treating the immune diseases through action to increase the activity of the Treg cells have been reported.

Further, in addition to the Treg cells, as another group created in the differentiation process, Th17 cells are included, and the Th17 cells are formed through a similar process to the differentiation of the Treg cells in the differentiation process of undifferentiated T cells. That is, the Treg cells and the Th17 cells are commonly differentiated in the presence of TGF-β, but in the case of the Treg cells, IL-6 is not required, whereas the Th17 cells are differentiated in the presence of IL-6 in addition to the TGF-β. Further, the differentiated Th17 cells are characterized by secreting IL-17.

It has been shown that the Th17 cells are involved in the forefront of the inflammatory response shown in the immune diseases unlike the Treg cells to maximize a signal of the inflammatory response and accelerate the progress of the diseases. Therefore, in the case of an autoimmune disease which is not controlled by the Treg cells among the autoimmune diseases, development of therapeutic agents for the autoimmune diseases targeting the inhibition of the Th17 cell activity has largely emerged.

However, as therapeutic agents for the immune diseases which have been currently used, immunosuppressive agents which block a signal transduction pathway in the T cells are most commonly used. There is a problem in that the immunosuppressive agents cause side effects such as toxicity, infection, lymphoma, diabetes, tremor, headache, diarrhea, hypertension, nausea, and renal dysfunction.

Further, even in addition to the method of treating the immune diseases by the method of inhibiting the activation of the T cells, a therapeutic method of adjusting an amount of cytokines secreted from immune cells and a therapeutic method using antibodies targeting cytokines secreted from the immune cells are being developed. However, until the method is actually applied to patients through clinical trials, a lot of time is required, and in the method using the antibodies, too much cost is required in the antibody producing process.

In this aspect, the novel compounds provided in the present invention has a function capable of operating simultaneously inhibition of the production of the inflammatory cytokines, inhibition of the Th17 cells, and the activity of the Treg cells to more efficiently treat the immune diseases than existing therapeutic agents.

Furthermore, when describing the result of the exemplary embodiment of the present invention, it may be verified that the compounds of the present invention has the activity of inhibiting the gene expression of STAT3. Recently, in various tumors, activated forms of STAT1, STAT3 and STAT5 has been found, and the STAT3 is activated in a variety of solid cancers such as breast cancer, head cancer, melanoma, ovarian cancer, lung cancer, pancreatic cancer, and prostate cancer as well as blood cancers such as leukemia to be an important anticancer target (Hua Yu and Richard Jove, Nature Review Cancer., 2004, 8, 945).

Further, it is known that the activity of STAT3 inhibits apoptosis, induces angiogenesis, and induces immune evasion (Wang T. et al., Nature Medicine., 2004, 10, 48). Accordingly, the inhibition of the STAT3 activity has an effect capable of controlling the tumors by a complex anti-cancer mechanism, and a STAT3 protein is involved in various cellular functions as well as the tumors and thus the discovery of inhibitors thereof can be developed as immunosuppressive agents.

Further, for reference, the immune system controls a specific immune response to an autoantigen in a normal state and inhibits an immune response to external antibodies, and for example, may include a response to fetus of pregnant women and an immune response to microorganisms in a chronic infection state. It is known that the phenomena are induced by clonal deletion, clonal anergy, and an active control by the immunoregulatory T cells (Treg) as a mechanism capable of inducing antigen-specific immune tolerance. When examining some patients in which the immune tolerance to transplantation antigens is incidentally acquired or an animal model in which the immune tolerance is experimentally induced, it is verified that all of the three mechanisms above are involved in transplantation immune tolerance. Particularly, recently, immunoregulatory T lymphocytes have received attention as important cells involved to control almost all of immune responses of living bodies such as autoimmunity, tumor immunity, and an infectious immune response as well as the transplantation immune response.

The immunoregulatory T cells, that is, the immunoregulatory T lymphocytes (Treg) of which existence has been recently found may be largely divided into natural Treg cells and adaptive Treg cells, and CD4+ CD25+ T cells as the natural Treg receive the immunosuppressive function from when the cells are newly produced in the thymus and are present at a frequency of 5 to 10% among peripheral CD4+ T lymphocytes in a normal individual. The immunosuppressive mechanism of the cells is not accurately determined up to now, but it is recently found that an expression control factor of a gene of Foxp3 plays an important role in the differentiation and the activity of the cells. Further, the peripheral natural T cells receive a stimulus of self or foreign antigens under a specific environment to be differentiated to cells having an immunosuppressive effect and called and adaptive or inducible Treg, and Tr1 secreting IL-10 and Th3, CD8 Ts, and the like secreting TGF-β correspond to the peripheral natural T cells.

Further, the T cells are also differentiated to Th17 cells through the differentiation process in addition to the Treg cells, and the Th17 cells are differentiated in the presence of the TGF-β in common with the Treg cells, but in the case of the Treg cells, the IL-6 is not required, whereas the Th17 cells are differentiated in the presence of IL-6 in addition to TGF-β and secret IL-17.

Further, the Th17 cells have cytotoxicity that accelerates the progress of the disease by maximizing the signal of the inflammatory response. Accordingly, the differentiation to the Th17 or the inhibition of the activity is one of methods for treating the immune diseases.

Further, the Treg cells express Foxp3 and the Foxp3 is mainly present in immunoregulatory T cells derived from the thymus and as a transcriptional factor which is present in cells having a CD4+CD25+ labeled antigen, the function has a low responsive to the antigen when recognizing the antigen to the T cells expressing the Foxp3 and simultaneously serves as suppressor T cells of suppressing production of IL-2 and cell division for the T cells which can potentially cause autoimmunity among the CD4+CD25-T cells without expressing the Foxp3 which are differentiated from the thymus. Further, it is found that the Foxp3 serves to suppress transcriptional regulation of IL-4, IFN-γ, and the like influenced by NFAT as a transcription factor as wells as IL-2 with respect to the regulatory T cells expressing the Foxp3 and CD25− T cells through a cell-cell contact therewith. Accordingly, in the case of the T cells expressing the Foxp3 functioned above, the T cells are applied to treat the immune diseases through an action of suppressing or regulating the immune response. Further, attempts to apply a self-antigen specific T cell clone of the CD4 T cells expressing the Foxp3 which is present in the human as a cell therapy method by increasing the number of the clones through treatment of high-concentration IL-2 cytokines and combination of anti-CD3 and anti-CD28 antibodies have been made.

Therefore, when describing a technical development status associated with existing treatment of immune diseases, the novel compounds provided in the present invention solve the problems which have not been solved in the related art and have more effective pharmacological effects and thus may be very useful as the agents for treating the immune diseases.

Therefore, the pharmaceutical composition for preventing or treating the immune diseases provided in the present invention may include the novel compound according to the present invention or a pharmaceutically acceptable salt thereof. The salt is preferably an acid addition salt formed by pharmaceutically acceptable free acid, and the free acid may use organic acid and inorganic acid. The organic acid is not limited thereto, but includes citric acid, acetic acid, lactic acid, tartaric acid, maleic acid, fumaric acid, formic acid, propionic acid, oxalic acid, trifluoroacetic acid, benzoic acid, gluconic acid, metasulfonic acid, glycolic acid, succinic acid, 4-toluenesulfonic acid, glutamic acid, and aspartic acid. Further, the inorganic acid is not limited, but includes hydrochloric acid, hydrobromic acid, sulfuric acid, and phosphoric acid.

The compound according to the present invention may be isolated from the natural or prepared by a chemical synthesis method known in the art, and the inventors synthesized and prepared the compounds by methods disclosed in the following Examples.

In the present invention, the "immune diseases" mean diseases in which components of the mammalian immune system cause, mediate, or contribute the pathological conditions of the mammals. Further, the immune diseases may include all of diseases in which simulation or the stop of the immune response has a compensating effect on the progression of the diseases, and in the present invention, may include diseases caused by hypersensitive immune responses. Examples of the immune diseases are not limited thereto, but may include autoimmune diseases; inflammatory diseases; and transplantation rejection diseases of cells, tissues or organs, and the like.

Further, in all normal subjects, one of the most important features has ability capable of recognizing, responding, and removing many non-self-antigens without harmfully responding to self-antigen substances. As such, a non-response to the self-antigen of the living body is called immunologic unresponsiveness or tolerance.

However, a disease caused by such a process that when a problem in inducing or continuously maintaining the self-tolerance occurs, the immune response to the self-antigen occurs, and thus a phenomenon in which the self-antigen attacks its tissue occurs is called an "autoimmune disease".

Further, the "inflammatory disease" means a disease caused by inflammatory substances (inflammatory cytokines) such as tumor necrosis factor-α (TNF-α), interleukin-1 (IL-1), IL-6, prostaglandin, leukotriene, or nitric oxide (NO) which is secreted from immune cells such as macrophagocyte by excessively accelerating the human immune system by inflammatory agents or injurious stimuli such as UV irradiation.

Further, for successful organ transplantation, a recipient's immune rejection response to cells and organs to be transplanted needs to be overcome. A major media of the immune rejection response in transplantation is T cells and a major histocompatibility complex (MHC) which is expressed in a graft is recognized by a T cell receptor and the immune response is induced and the rejection response in transplantation occurs. The MHC is determined according to a type of glycoprotein antigen, and an immune response which occurs when a histocompatibility antigen is not matched is an obstacle to block the successful transplantation and thus the accuracy of a histocompatibility antigen test and investigation of matches are very important elements.

The human includes many types of histocompatibility antigens, and includes Class I antigens including HLA-A, -B, and -C and Class II antigens HLA-DR, -DP, and -DQ. A biological function of these antigens is to deliver the antigens to T lymphocytes, and the Class I antigens are expressed in most of nucleated cells and the antigens delivered therethrough are recognized by CD8+ cytotoxic T lymphocytes. The Class II antigens are expressed in dendritic cells, B lymphocytes, activated T lymphocytes, macrophages, and the like which are known as antigen-presenting cells and have a function to deliver the antigen to CD4+ T lymphocytes. The T lymphocytes recognize the antigens by binding the antigens delivered to the T lymphocytes to the T lymphocyte receptor and recognize the histocompatibility antigens derived from another person other than one's own in the transplantation process at a high frequency. About 1 to 10% of the entire T lymphocytes of a donor or a patient recognize the histocompatibility antigens derived from the patient or the donor to be proliferated by the response thereto and cause a series of immune responses, and it is called an "alloresponse". Further, the T lymphocytes of the donor cause the immune response to the histocompatibility antigen of the patient and it is called a "graft-versus-host disease (GVDH)", and on the contrary, a response to the histocompatibility antigen of the donor caused by the T lymphocytes of the patient is called a "graft rejection response".

Accordingly, in order to reduce an abnormal response by the immune response generated in the grafting process, immunosuppressive agents have been used, and the common object of the immunosuppressive agents is to suppress the T cell-mediated immune response to the graft. Recently, a method to treat graft rejection diseases by suppressing the immune response using the regulatory T cells has been attempted.

Further, the types of immune diseases which can be prevented and treated in the present invention are not limited thereto, but may include rheumatoid arthritis, Behcet's disease, multiple myositis or skin myositis, autoimmune hematocytopenia, autoimmune myocarditis, atopic dermatitis, asthma, primary cirrhosis, dermatomyositis, Goodpasture syndrome, autoimmune meningitis, sjogren's syndrome, lupus, Addison's disease, alopecia areata, ankylosing myelitis, autoimmune hepatitis, autoimmune mumps, Crohn's disease, insulin-dependent diabetes, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, sarcoidosis, scleroderma, spinal arthrosis, thyroiditis, vasculitis, vitiligo, myxedema, pernicious anemia, mitochondrial-related syndromes, ulcerative colitis, and the like.

Therefore, the composition according to the present invention may be used as a pharmaceutical composition capable of preventing or treating the immune diseases.

Unless otherwise specified, the term 'treatment' means that a disease, a disorder, or one or more symptoms of the disease or the disorder to which the term is applied is reversed or alleviated, or the progress thereof is inhibited or prevented, and the term 'treatment' used in the present invention means a treating action defined as described above. Accordingly, the "treatment" or the "treating method" of the immune diseases in mammals may include one or more treatments below of:

(1) inhibiting a growth of the immune diseases, that is, preventing the development, (2) preventing the spread of the immune diseases, that is, preventing metastasis, (3) reducing the immune diseases, (4) preventing recurrence of the immune diseases, and (5) palliating symptoms of the immune diseases.

The composition for preventing or treating the immune diseases according to the present invention may include one or more types of compounds among the novel compounds or a salt thereof with a pharmaceutically effective amount alone or include one or more carriers, excipients, or diluents which are pharmaceutically acceptable. The pharmaceutically effective amount means an amount sufficient to prevent, improve, and treat the symptoms of the immune diseases.

The pharmaceutically effective amount of the novel compound or the salt thereof according to the present invention may be properly changed according to the degree of the symptom of the immune disease, an age, a weight, a health state, a sex, an administration route, and a treatment period of a patient, and the like.

Further, the above "pharmaceutically acceptable" generally means a composition which does not cause an allergic reaction such as gastroenteric trouble and dizziness or a similar reaction thereto when being physiologically acceptable and administered to the human body. Example of the carriers, the excipients, and the diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, and mineral oil. Further, a filler, an anti-coagulant, a lubricant, a wetting agent, a flavoring, an emulsifier, a preservative, and the like may be additionally included.

Further, the composition of the present invention may be formulated by using a known method in the art so as to provide rapid, sustained, or delayed release of an active component after being administrated to the mammal. The formulation may be a form of a powder, granules, a tablet, an emulsion, a syrup, an aerosol, a soft or hard gelatin capsule, a sterile injection solution, and a sterile powder.

Further, the composition for preventing or treating the immune diseases according to the present invention may be administrated through various routes including oral, percutaneous, subcutaneous, intravenous and intramuscular tissues, and the administration amount of the active component may be properly selected according to various factors such as an administration route, an age, a sex, and a weight of a patient, and the severity of the patient. The composition for preventing or treating the immune diseases according to the present invention may be administrated by combining a known compound having an effect of preventing, improving, or treating the symptoms of the immune diseases.

The present invention also provides a use of the composition containing the compound as an active ingredient for preparing drugs for preventing or treating the immune diseases. The composition containing the compound as the active ingredient according to the present invention may be used for preparing the drugs for preventing or treating the immune diseases.

The present invention also provides a method for preventing or treating immune diseases including administrating the pharmaceutical composition of the present invention to the mammal with a therapeutically effective amount.

The term "mammal" used herein means a mammal which is a target for treatment, observation, or testing, and preferably, the human.

The term "therapeutically effective amount" used herein means an amount of an active ingredient or a pharmaceutical composition which induces a biological or medical response in a tissue system considered by researchers, veterinarian, physician, or other clinicians, an animal, or the human and includes an amount of inducing alleviation of symptoms of diseases or disorders to be treated. It is apparent to those skilled in the art that an effective dose and the number of administration times on the treatment for the ingredient component of the present invention are changed according to a desired effect. Therefore, an optimal dose to be administrated may be easily determined by those skilled in the art, and may be adjusted according to various factors including a type of disease, severity of the disease, the contents of an active ingredient and other ingredients contained in the composition, a type of formulation, and an age, a weight, a general health status, a sex, a diet, an administration time, a route of administration, a secretion ratio of the composition, a treating period, and simultaneously used drugs.

Furthermore, the present invention may provide an immune regulatory agent containing the compound provided in the present invention as an active ingredient.

Further, the present invention may provide a method of decreasing the activity of Th17 cells in the cells by treating the compound of the present invention in the cells in vitro and also provide a method of increasing the activity of Treg cells in the cells by treating the novel compound of the present invention in the cells in vitro.

BEST MODE

Hereinafter, the present invention will be described in more detail through Examples. Examples are to describe the present invention in detail and the scope of the present invention is not limited to Examples.

Example 1

Synthesis of Novel Compound Having Effect of Treating Immune Diseases According to the Present Invention The novel compounds represented by chemical formulas in the following Table 1 were prepared by a method of the following reaction formula. In detail, first, in a sealed reactor, an aniline compound of 1.0 mmol was dissolved in an acetonitrile solvent and then added with 1.0 mmol dicyandiamide and 1.0 mmol concentrated sulfuric acid, sealed, and stirred for 1 hr at 175° C. Thereafter, the solution was cooled at room temperature to produce a white solid and washed by hexane and isopropyl alcohol after the solvent was removed to synthesize the following compounds having a white solid form.

In processes for synthesizing a total of 24 compounds, other compounds except for an aniline compound were synthesized under the same condition, and a kind of aniline used for the synthesis of each compound and chemical names and structural formulas of the synthesized compounds are as disclosed in the following Table.

A representative reaction formula used for synthesizing the compounds is as illustrated below.

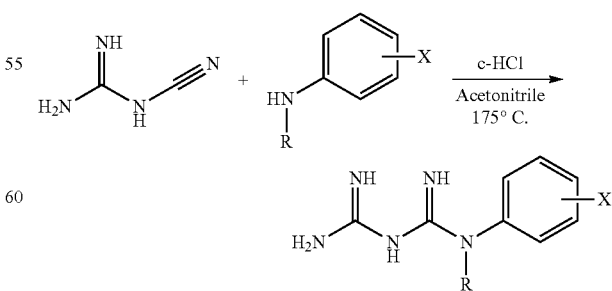

Dicyanodiamide Aniline In the reaction formula, R is alkyl and X is at least one of F, Cl, or Br.

TABLE 1

| Compound Code | Compound Name | Used Aniline | Compound Structure |
|---|---|---|---|
| SD-281 | N-(3,4-Difluorophenyl)-N-ethylbiguanide | 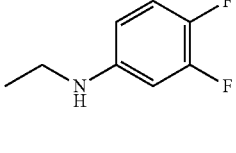 | 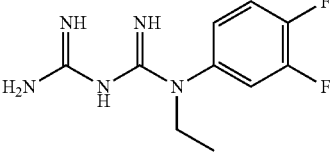 |
| SD-282 | N-Ethyl-N-(4-fluorophenyl)biguanide | 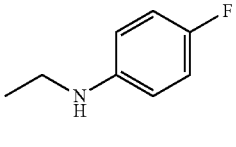 | 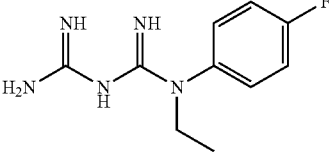 |
| SD-283 | N-(2,4-Difluorophenyl-N-ethylbiguanide | 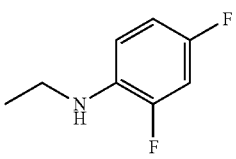 | 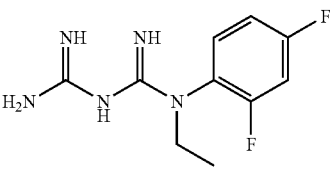 |
| SD-284 | N-(2,4-Difluorophenyl)-N-methyl)biguanide | 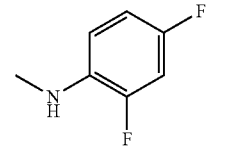 | 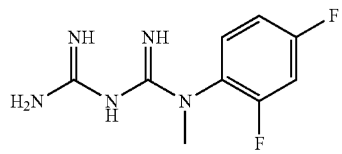 [SMILES: CN(C(=N)NC(=N)N)c1ccc(F)cc1F] |
| SD-562 | N-(4-Chlorophenyl)biguanide | 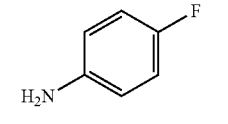 | 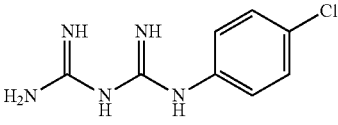 |
| SD-563 | N-(4-Bromophenyl)biguanide | 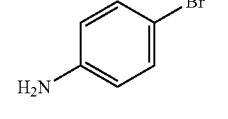 | 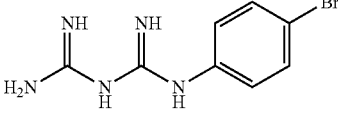 |
| SD-564 | N-(3-Chlorophenyl)biguanide | 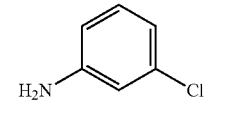 | 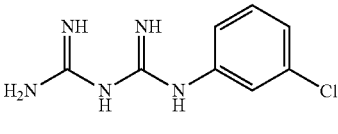 [SMILES: N=C(N)NC(=N)Nc1cccc(Cl)c1] |
| SD-565 | N-(3-Bromophenyl)biguanide | 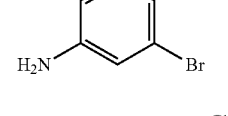 | 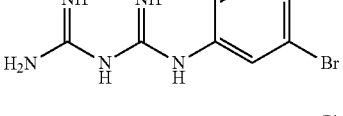 |
| SD-566 | N-(4-Chlorophenyl)-N-ethylbiguanide | 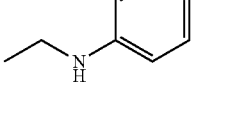 | 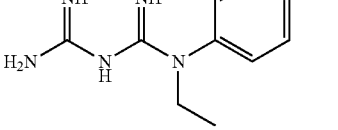 |
| SD-567 | N-(4-Bromophenyl)-N-ethylbiguanide | 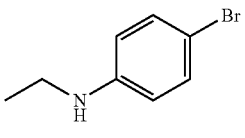 | 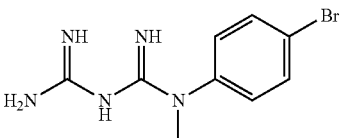 |

TABLE 1-continued

| Compound Code | Compound Name | Used Aniline | Compound Structure |
|---|---|---|---|
| SD-568 | N-(3-Chlorophenyl)-N-ethylbiguanide | | 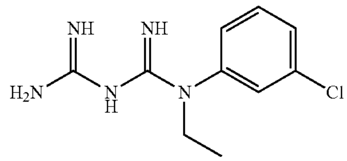 |
| SD-569 | N-(3-Bromophenyl)-N-ethylbiguanide | | 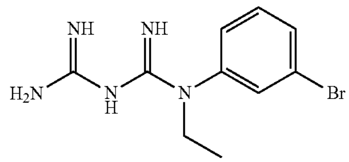 [SMILES: CCN(C(=N)NC(=N)N)c1cccc(Br)c1] |
| SD-570 | N-Phenylbiguanide | | 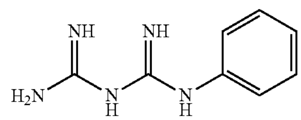 [SMILES: N=C(N)NC(=N)Nc1ccccc1] |
| SD-571 | N-(3,5-Difluorophenyl)biguanide | | 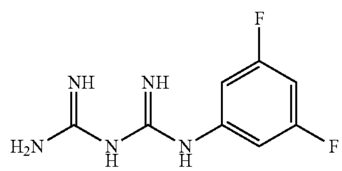 [SMILES: N=C(N)NC(=N)Nc1cc(F)cc(F)c1] |
| SD-572 | N-(3,4-Difluorophenyl)biguanide | | 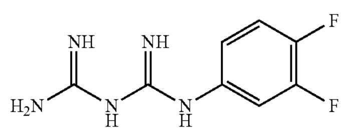 [SMILES: N=C(N)NC(=N)Nc1ccc(F)c(F)c1] |
| SD-573 | N-Ethyl-N-phenyl biguanide | | 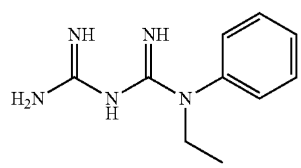 |
| SD-574 | N-Ethyl-N-(2-fluorophenyl)biguanide | | 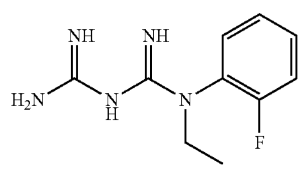 [SMILES: CCN(C(=N)NC(=N)N)c1ccccc1F] |
| SD-575 | N-Ethyl-N-(3-fluorophenyl) biguanide | | 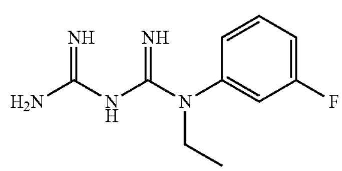 [SMILES: CCN(C(=N)NC(=N)N)c1cccc(F)c1] |
| SD-576 | N-(3,5-Difluorophenyl)-N-ethylbiguanide | | 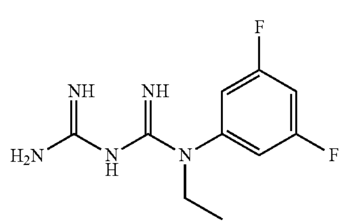 [SMILES: CCN(C(=N)NC(=N)N)c1cc(F)cc(F)c1] |

TABLE 1-continued

| Compound Code | Compound Name | Used Aniline | Compound Structure |
|---|---|---|---|
| SD-577 | N-(2,5-Difluorophen-yl)-N-ethylbiguanide | 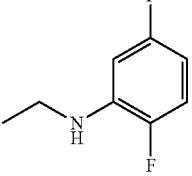 | 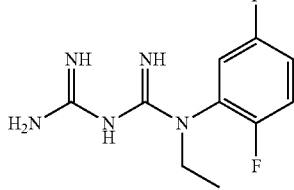 |
| SD-578 | N-Ethyl-N-(2,3,4-tri fluorophenyl) biguanide | 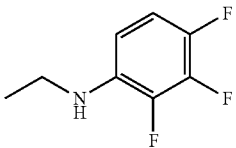 | 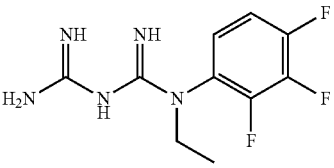 |
| SD-579 | N-Phenyl-N-isopropyl-biguanide | 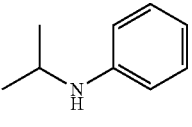 | 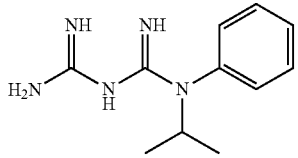 [SMILES: CC(C)N(C(=N)NC(=N)N)c1ccccc1] |
| SD-580 | N-(2,4-Difluorophen-yl)-N-propylbiguanide | 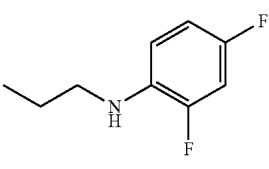 | 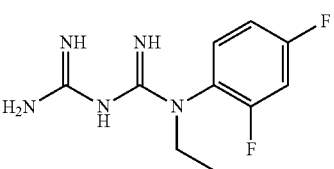 |
| SD-581 | N-(4-Difluorophen-yl)-N-propylbiguanide | 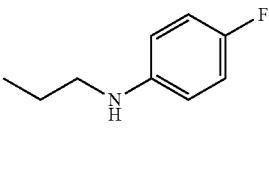 | 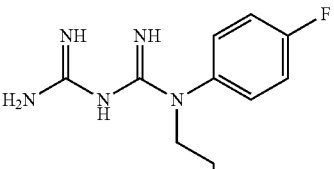 |

With respect to derivative compounds of the present invention synthesized by the above method, each compound was identified by $^1$H-NMR assay and the result thereof is as described in the following Table.

TABLE 2

| Compound Code | Chemical Name | Result of NMR analysis |
|---|---|---|
| SD-281 | N-(3,4-Difluorophenyl)-N-ethylbiguanide | $^1$H NMR(600 MHz, DMSO-$d_6$) δ(ppm): 8.13(bs, 2H), 7.47-7.39(m, 2H), 7.26-7.16(m, 2H), 6.98(bs, 3H), 3.62(q, J = 7.2 Hz, 2H), 1.03(t, J = 7.2 Hz, 3H) MS [M + H]$^+$242.2 |
| SD-282 | N-Ethyl-N-(4-fluorophenyl)biguanide | $^1$H NMR(600 MHz, DMSO-$d_6$) δ(ppm): 7.36-7.34 (m, 2H), 7.30(t, J = 6.6 Hz, 2H), 7.10(bs, 2H), 6.85(bs, 4H), 3.68(q, J = 7.2 Hz, 2H), 1.06(t, J = 7.2 Hz, 3H) MS [M + H]$^+$224.6 |
| SD-283 | N-(2,4-Difluorophenyl)-N-ethylbiguanide | $^1$H NMR(600 MHz, DMSO-$d_6$) δ(ppm): 7.50-7.42(m, 3H), 7.25-7.18(m, 2H), 7.02(bs, 4H), 3.66(q, J = 7.2 Hz, 2H), 1.06(t, J = 7.2 Hz, 3H) MS [M + H]$^+$242.2 |
| SD-284 | N-(2,4-Difluorophenyl)-N-methylbiguanide | $^1$H NMR(600 MHz, DMSO-$d_6$) δ(ppm): 7.56-7.52(m, 1H), 7.39-7.36(m, 2H), 7.17-7.14(m, 5H), 6.79(s, 1H), 3.22(s, 3H) MS [M + H]$^+$228 |

TABLE 2-continued

| Compound Code | Chemical Name | Result of NMR analysis |
|---|---|---|
| SD-562 | N-(4-Chlorophenyl)biguanide | $^1$H NMR(600 MHz, DMSO-d$_6$) δ(ppm): 9.86 (s, 1H), 7.39-7.32(m, 8H), 7.06(bs, 2H) MS [M + H]$^+$212.6 |
| SD-563 | N-(4-Bromophenyl)biguanide | $^1$H NMR(600 MHz, DMSO-d$_6$) δ(ppm): 9.84(s, 1H), 7.46-7.44(m, 2H), 7.36-7.33(m, 6H), 7.06(bs, 2H) MS [M + H]$^+$257.1 |
| SD-564 | N-(3-Chlorophenyl)biguanide | $^1$H NMR(600 MHz, DMSO-d$_6$)δ(ppm): 9.81(s, 1H), 7.55(s, 1H), 7.39(bs, 3H), 7.29(t, J = 7.8 Hz, 1H), 7.24(d, J = 7.8 Hz, 1H), 7.08-7.06(m, 3H) MS [M+H]$^+$212.6 |
| SD-565 | N-(3-Bromophenyl)biguanide | $^1$H NMR(600 MHz, DMSO-d$_6$) δ(ppm): 9.78(s, 1H), 7.67(bs, 1H), 7.38(bs, 3H), 7.29(d, J = 7.8 Hz, 1H), 7.23(t, J = 7.8 Hz, 1H), 7.20-7.19(m, 1H), 7.05(bs, 2H) MS [M + H]$^+$257.1 |
| SD-566 | N-(4-Chlorophenyl)-N-ethylbiguanide | $^1$H NMR(600 MHz, DMSO-d$_6$)δ(ppm): 7.49(d, J = 6.6 Hz, 2H), 7.30(d, J = 6.6 Hz, 2H), 7.28(bs, 2H)7.06(bs, 4H), 3.68(q, J = 7.2 Hz, 2H)1.04(t, J = 7.2 Hz, 3H) MS [M + H]$^+$240.7 |
| SD-567 | N-(4-Bromophenyl)-N-ethylbiguanide | $^1$H NMR(600 MHz, DMSO-d$_6$)δ(ppm): 7.60(d, J = 6.9 Hz, 2H), 7.23(d, J = 6.9 Hz, 2H), 7.16(bs, 2H)7.00(bs, 4H), 3.68(q, J = 7.2 Hz, 2H), 1.03(t, J = 7.2Hz, 3H) MS [M + H]$^+$285.2 |
| SD-568 | N-(3-Chlorophenyl)-N-ethylbiguanide | $^1$H NMR(600 MHz, DMSO-d$_6$)δ(ppm): 7.43(t, J = 7.8 Hz, 1H), 7.40(t, J = 1.8 Hz, 1H), 7.38-7.36(m, 1H)7.20-7.24(m, 1H), 7.23(bs, 2H), 6.96(bs, 4H)3.68(q, J = 7.2 Hz, 2H), 1.04(t, J = 7.2 Hz, 3H) MS [M + H]$^+$240.7 |
| SD-569 | N-(3-Bromophenyl)-N-ethylbiguanide | $^1$H NMR(600 MHz, DMSO-d$_6$)δ(PPm): 7.53(t, J = 2.4 Hz, 1H), 7.51-7.49(m, 1H), 7.37(t, J = 7.8 Hz, 1H)7.30-7.28(m, 2H), 7.19(bs, 2H), 7.09(bs, 1H), 6.97(bs, 3H), 3.68(q, J = 7.2 Hz, 2H)1.04(t, J = 7.2 Hz, 3H) MS [M + H]$^+$285.2 |
| SD-570 | N-Phenylbiguanide | $^1$H NMR(600 MHz, DMSO) δ(ppm): 9.504(s, 1H), 7.33(d, J = 7.8 Hz, 2H), 7.28(t, J = 7.2 Hz, 2H), 7.229(bs, 3H), 7.034(t, J = 7.2 Hz, 1H), 6.989(bs, 2H); MS [M + H]$^+$ 178.2 |
| SD-571 | N-(3,5-Difluorophenyl)biguanide | $^1$H NMR(600 MHz, DMSO) δ(ppm): 10.25(s, 1H), 7.57(bs, 4H), 7.19-7.11(m, 4H), 6.88-6.84(m, 1H) MS [M + H]$^+$214.2 |
| SD-572 | N-(3,4-Difluorophenyl)biguanide | $^1$H NMR(600 MHz, DMSO) δ(ppm): 10.08(s, 1H), 7.62-7.59(m, 1H), 7.48(s, 4H), 7.42-7.32(m, 1H), 7.12(bs, 3H) MS [M + H]$^+$214.2 |
| SD-573 | N-Ethyl-N-phenylbiguanide | $^1$H NMR(600 MHz, DMSO) δ(ppm): 8.95(t, J = 7.2 Hz, 2H), 8.84(t, J = 6.6 Hz, 1H)8.80(t, J = 7.2 Hz, 2H), 8.57(bs, 2H), 8.42(s, 4H), 5.21(q, J = 7.2 Hz, 2H), 2.57(t, J = 7.2 Hz, 3H) MS [M + H]$^+$206.2 |
| SD-574 | N-Ethyl-N-(2-fluorophenyl)biguanide | $^1$H NMR(600 MHz, DMSO) δ(ppm): 7.39(t, J = 7.8 Hz, 2H), 7.32(t, J = 9 Hz, 2H)7.26(t, J = 7.2 Hz, 2H), 6.92(s, 4H), 3.65(q, J = 7.2 Hz, 2H), 1.04(t, J = 7.2 Hz, 3H) MS [M + H]$^+$224.2 |
| SD-575 | N-Ethyl-N-(3-fluorophenyl)biguanide | $^1$H NMR(600 MHz, DMSO) δ(ppm): 7.45(q, J = 7.2 Hz, 1H), 7.22-7.13(m, 5H)7.023(s, 4H), 3.704(q, J = 7.2 Hz, 2H), 1.05(t, J = 7.2 Hz, 3H) MS [M + H]$^+$224.2 |
| SD-576 | N-(3,5-Difluorophenyl)-N-ethylbiguanide | $^1$H NMR(600 MHz, DMSO) δ(ppm): 7.28(s, 2H), 7.22-7.19(m, 1H) 7.11(dd, J$_1$ = 7.8 Hz, J$_2$ = 2.4 Hz, 2H), 7.02(s, 4H), 3.71(q, J = 7.2 Hz, 2H), 1.05(t, J = 7.2 Hz, 3H) MS [M + H]$^+$242.2 |
| SD-577 | N-(2,5-Difluorophenyl)-N-ethylbiguanide | $^1$H NMR(600 MHz, DMSO) δ(ppm): 7.40-7.24(m, 5H), 7.07(s, 4H) 3.71(q, J = 7.2 Hz, 2H), 1.04(t, J = 7.2 Hz, 3H)' MS [M+H]$^+$242.2 |
| SD-578 | N-Ethyl-N-(2,3,4-trifluorophenyl)biguanide | $^1$H NMR(600 MHz, DMSO) δ(ppm): 7.41(q, J = 9 Hz, 1H), 7.32-7.29(m, 2H), 7.14(s, 5H)3.65(q, J = 7.2 Hz, 2H), 1.04(t, J = 7.2 Hz, 3H) MS [M+H]$^+$260.2 |

TABLE 2-continued

| Compound Code | Chemical Name | Result of NMR analysis |
|---|---|---|
| SD-579 | N-Phenyl-N-isopropyl-biguanide | $^1$H NMR(600 MHz, DMSO) δ(ppm): 7.48(t, J = 7.2 Hz, 2H), 7.43(t, J = 7.2 Hz, 1H), 7.22(d, J = 7.2 Hz, 2H), 7.05(s, 1H), 6.85(s, 3H), 6.73(s, 2H), 4.69(t, J = 6.6 Hz, 1H), 0.98(d, J = 6.6 Hz, 6H) MS [M + H]$^+$220.3 |
| SD-580 | N-(2,4-Difluorophenyl)-N-propylbiguanide | $^1$H NMR(600 MHz, DMSO) δ(ppm): 7.47-7.35(m, 3H), 7.26-7.15(m, 2H), 6.99(s, 4H), 3.53(t, J = 7.2 Hz, 2H), 1.45(m, 2H), 0.80(t, J = 7.2 Hz, 3H) MS[M + H]$^+$256.3 |
| SD-581 | N-(4-Difluorophenyl)-N-propylbiguanide | $^1$H NMR(600 MHz, DMSO) δ(ppm): 7.36-7.33(m, 2H), 7.29-7.26(m, 2H), 7.12(s, 3H), 6.94(s, 3H) 3.59(t, J = 7.8 Hz, 2H), 1.49-1.43(m, 2H), 0.82(t, J = 7.8 Hz, 3H) MS [M + H]$^+$238.2 |

<Testing Method>
<1> Cells to be Analyzed

The inventors performed the following test on the basis of the following test groups in order to verify whether the respective compounds newly synthesized in the present invention can treat and prevent immune diseases.

TABLE 3

Test groups performed in test of the present invention

| Test group | Test target cells |
|---|---|
| Normal mouse group | Spleen and BM cells of normal mouse DBA1J mouse |
| Rheumatoid arthritis mouse group | Spleen and BM cells of DBA1J mouse in which rheumatoid arthritis is induced by CIA |
| Lupus mouse group | Spleen and BM cells of sanroque mouse with lupus |
| Human P.B group | Lymphocytes isolated from human peripheral blood (P.B) |

More particularly, the normal mouse group was used after spleen cells obtained from a DBA/1J-based normal mouse was incubated for 72 h in an anti-CD3 0.5 μg/ml stimulation condition before being treated with the compounds of the present invention to be activated.

Further, the rheumatoid arthritis mouse was prepared by using the DBA/1J-based normal mouse, and in the normal mouse, Type 2 collagen CII was dissolved in a 0.1N acetic acid solution to be 4 mg/ml, dialyzed with a dialysis buffer (50 mM Tris, 0.2N Nacl), and mixed with the same amount as a complete Freund's adjuvant (CFA, Chondrex) containing M. tuberculosis, and then subcutaneously injected in the tail base of the mouse and an immunogen of 100 μl (that is, 100 μl/100 μg) per head was injected (primary injection). After two weeks from this, the same CII was mixed with the same amount of incomplete Freund's adjuvant (IFA, Chondrex) and 100 μl (that is, 100 μl/100 μg) was secondarily injected in one hind leg (foot pad) to prepare a mouse to develop rheumatoid arthritis, and spleen cells were obtained from the prepared rheumatoid arthritis mouse and used and also incubated for 72 h under an anti-CD3 0.5 μg/ml stimulation condition, and then activated and used.

Further, in a lupus-developed mouse model, a sanroque mouse used in a lupus model in the art was used and the human P.B group was used by obtaining lymphocytes from the human peripheral blood. The isolation of spleen cells and the isolation of lymphocytes from each mouse and the human peripheral blood were performed by a general method which was widely known in the art and the obtained cells were incubated for 72 h under the anti-CD3 0.5 μg/ml stimulation condition, activated, and then used.

<2> Cytotoxicity Analysis (MTT Assay)

In order to verify whether the compounds synthesized in the present invention causes the cytotoxicity in the cells, an MTT assay was performed, target cells were divided to be the number of 2×10$^5$ cells per well on a 96 well plate, treated with the compounds of the present invention for each concentration, incubated for 72 hrs, added with an MTT solution (0.5% 3-4,5-dimethyl thiazol-2-yl)-2,5-diphenyl-2H-tetrazolium bromide), and incubated for 4 hrs again. Thereafter, absorbance at 540 nm was measured by an enzymelinked immunospecific assay (ELISA) meter to observe the cytotoxicity.

<3> Analysis for Autoantibody Production and Immune Response Regulation

In order to verify whether the novel compound of the present invention has an effect on the production of Total IgG, Total IgG1, and IgG2a antibodies in the serum, the ELISA was performed. Accordingly, Total IgG and antibody-specific IgG1 and IgG2a were measured by using a sandwich ELISA by targeting the cells treated with the compound of the present invention. Monoclonal anti-mouse IgG and CII reacted for 1 hr at room temperature in the 96-well plate and then non-specific binding was blocked by a blocking solution (1% BSA/PBST). The mouse control serum was continuously diluted by ½ to be used as a standard and reacted for 1 hr at room temperature by adding a cell culture supernatant. Thereafter, anti-mouse IgG-HRP and anti-mouse IgG2a-HRP reacted for 1 hr at room temperature, washed four times, and colored with a TMB system, and the absorbance at a wavelength of 450 nm was measured.

<4> Analysis of Effect on Production of Inflammatory Cytokines

In order to verify whether the novel compounds of the present invention have an effect on inflammation and the production of inflammatory cytokines as cause substances of the immune diseases, the inventors analyzed the production degree of IL-17, IL-6, TNF-α, IFN-γ, MMP-9, and STAT-3 and the expression degree of mRNA of these cytokines by targeting each test group. The production degree of the inflammatory cytokines was analyzed through an ELISA after obtaining a supernatant by targeting cells which were treated with the compound of the present invention and incubated, and particularly, the cells reacted with cytokine-specific antibodies anti-IL-17, anti-IL-6, anti-TNF-α, anti-IFN-γ, anti-MMP-9, and anti-STAT-3 all night at 4 and then non-specific binding was blocked with a blocking solution (1% BSA/PBST). Thereafter, each biotinylated antibody was reacted at room temperature for 2 hrs, washed four times, and then reacted at room temperature for 2 hrs after diluting and adding an extravidin-alkaline phosphatase conjugate. Thereafter, a PNPP/DEA solution was added and colored, and then the absorbance was measured at a wavelength of 405 nm.

Further, in the analysis of the expression degree of the inflammatory cytokines, the amount of mRNA was analyzed by performing RT-PCR using a primer which was specifically bound to IL-17, IL-6, TNF-α and IFN-γ after obtaining total RNA from analysis-targeted cells.

<5> Analysis of Inhibition of Th 17 Cells and Treg Cell-Induced Activity

Furthermore, the inventors analyzed the novel compounds of the present invention by using a flow cytometer in order to verify whether the differentiation and activity of the Th17 cells associated with the induced inflammation can be inhibited and simultaneously the activity of the Treg cells having immune regulation ability can be promoted. That is, after the cells were incubated in a Th 17 cell or Treg cell differentiation condition targeting T cells, the number of Foxp3+ Treg cells or il-17+ Th 17 cells was analyzed through the flow cytometer.

<6> Effect of Inhibiting Differentiation of Osteoclasts

In the process of differentiating the osteoclasts, in order to examine the effect of the novel compound of the present invention, bone marrow cells of the mouse were obtained and the bone marrow cells were induced to be differentiated in the presence of a macrophage colony-stimulating factor (MCSF) and a soluble RANKL (see a method in Sugatani et al. 2003, J. Cell. Biochem. 90, 59-67). The bone marrow cells were prepared from the femur and the tibia of a 6-week-old mouse and left in the presence of M-CSF (30 ng/ml:R&D Systems, Minneapolis, Minn.) in a 8-hole chamber slide ($3 \times 10^5$ cells/hole; Nalge Nunc International, Naperville, Ill.) at 37° C., after 3 days, non-adhesive cells containing the lymphocytes were removed, and precursor cells of adhesive osteoclasts were added in the presence of M-CSF (30 ng/ml) and RANKL (30 ng/ml; Strathmann, Hamburg, Germany) and incubated for 4 days to obtain the osteoclasts. In this case, a cell culture medium was exchanged once while the M-CSF and the RANKL were added. The cells were fixed and straining was performed according to a protocol of a manufacturer by using a strain kit (sigma) with respect to tartrate-resistant acid phosphatase (TRAP). In each chamber, when the cells were observed by a microscope with 40 magnification, TRAP positive multinuclear cells containing three or more nuclei were counted as the osteoclasts (Sugatani. et al. 2003, J. Cell. biochem. 90, 59-67).

Further, the bone marrow cells were differentiated to the osteoclasts, the novel compound of the present invention was treated for each concentration in the presence of M-CSF and the RANKL, cultured for 48 hrs, and then the cells were strained by TRAP and TRAP positive multinuclear cells were counted.

Experimental Example 1

Analysis Result of Cytotoxicity of Novel Compounds According to the Present Invention In order to verify whether the novel compounds synthesized in Example 1 have the cytotoxicity, a cell survival rate was verified through the MTT assay by targeting cells in each test group disclosed in Table 3 above. That is, the cells of each test group were divided according to the number of $2 \times 10^5$ cells per well and treated with the novel synthesized compounds of the present invention for each concentration, and the cell survival rate was analyzed.

As a result, in SD-281, SD-282, SD-283, and SD-284 compounds, it can be seen that when compared with a control group or a metformin-treated group, the cytotoxicity was not observed according to treatment for each cell concentration and the compounds had no cytotoxicity according to normal cells and disease-group cells.

Experimental Example 2

Result of Effect on Autoantibody Production and Immune Response Regulation of Novel Compounds According to the Present Invention In order to examine an effect on an immune response by producing auto-antibodies of the novel compounds synthesized in Example 1, the blood was obtained from each mouse group through orbital bleeding from mice in the four groups described above and the serum was isolated from the blood, and the amount of IgG, IgG1, and IgG2a was measured.

As a result, in the compounds of the present invention, it was shown that the amount of immunoglobulin (total IgG, IgG1, and IgG2) which was in the auto-antibody production state under the disease condition was reduced for each processing concentration of the compound, and it can be seen that in compounds disclosed in the following Table 4, an immunoregulatory function of inhibiting excessive immune response was excellent.

TABLE 4

| | Total IgG | | | IgG1 | | | IgG2 | | |
|---|---|---|---|---|---|---|---|---|---|
| | A | B | C | A | B | C | A | B | C |
| Control group | 11 | 83.2 | 141.5 | 311.4 | 286 | 422.3 | 103.2 | 109.6 | 151.9 |
| SD-281 | 2.3 | 58.1 | 124.5 | 83.8 | 135.2 | 258.2 | 35.6 | 33.5 | 84.3 |
| SD-282 | 0.7 | 60.3 | 127.7 | 1 | 218.7 | 425.4 | 37.1 | 38.3 | 110.9 |
| SD-283 | 2.9 | 49.6 | 113.5 | 41 | 135.3 | 296.5 | 97.6 | 99.4 | 76 |

Unit: ng/ml
A: Normal mouse cells,
B: Rheumatoid arthritis cells,
C: Lupus cells,
D: Lymphocytes of human peripheral blood Experimental Example 3

Analysis Result of Production of Inflammatory Cytokines and Inhibition of Gene Expression A test for verifying whether the novel compounds of the present invention inhibit the production of the inflammatory cytokines inducing the inflammation and immune diseases and inhibit these factors at a gene level was performed by a method described in the analysis of the effect on the production of the inflammatory cytokines disclosed in the <4>.

As the analyzed result, all of the novel compounds synthesized in the present invention inhibited the production of IL-17, IL-6, TNF-α, IFN-γ, MMP-9, and STAT-3 which were the inflammatory cytokines and the expression at the gene level to be process concentration dependent. Accordingly, through the result, it can be seen that the novel compounds synthesized in the present invention can prevent and treat the immune diseases by inhibiting the production of the inflammatory cytokines.

TABLE 5

Analysis of effect on production of inflammatory cytokines of novel compounds according to the present invention

| | IL-17 | | | | IL-6 | | | | TNF-a | | | | IFN-r | | | |
|---|---|---|---|---|---|---|---|---|---|---|---|---|---|---|---|---|
| | A | B | C | D | A | B | C | D | A | B | C | D | A | B | C | D |
| control | 3.2 | 3.7 | 0.9 | 0.3 | 2.2 | 1.9 | 1.8 | | 0.9 | 0.1 | 1.3 | | 9.4 | 8.3 | 14.5 | 0.2 |
| SD-2.81 | 1.7 | 2.2 | 0.6 | 0.1 | 1.4 | 1.4 | 1 | | 0.5 | 0.4 | 0.7 | | 5.8 | 5.3 | 10 | 0.1 |
| SD-2.82 | 1.7 | 2.1 | 0.6 | 0.1 | 1.3 | 1.3 | 1 | | 0.4 | 0.4 | 0.7 | | 3.3 | 2.9 | 7.6 | 0.1 |
| SD-2.83 | 1.6 | 2.2 | 0.4 | 0.1 | 1.4 | 1.1 | 0.9 | | 0.5 | 0.3 | 0.6 | | 7.2 | 5.4 | 5.5 | 0.1 |
| SD-2.84 | | | | 0.1 | | | | | | | | | | | | 0.08 |

Unit: ng/ml
A: Normal mouse cells,
B: Rheumatoid arthritis cells,
C: Lupus cells,
D: Lymphocytes of human peripheral blood

TABLE 6

Analysis of effect on production of inflammatory cytokines by targeting normal mouse cells of SD-284 compound

| | IL-17 | IL-6 | TNF-a | IFN-r |
|---|---|---|---|---|
| Control group | 7.6 | 1.8 | 0.7 | 10 |
| SD-284 | 6.5 | 0.7 | 0.5 | 4.9 |

Unit: ng/ml

TABLE 7

Analysis of inhibition of activity of inflammatory factor of compound of the present invention

| | TNF-a | | | MMP-9 | | | STAT3 |
|---|---|---|---|---|---|---|---|
| | A | B | C | A | B | C | A |
| control | 1 | 1 | 1 | 1 | 1 | 1 | 1 |
| SD-281 | 0.2 | 0.6 | 0.1 | 0.5 | 0.4 | 0.4 | 1.2 |
| SD-282 | 0.07 | 0.06 | 0.8 | 0.1 | 0.08 | 1.3 | 0.6 |
| SD-283 | 0.4 | 0.06 | 0.1 | 0.3 | 1 | 0.04 | 1.3 |

Unit: gene expression
A: Normal mouse cells,
B: Rheumatoid arthritis cells,
C: Lupus cells

TABLE 8

Analysis of effect on inhibition of Th17 and activity of Treg of compounds according to the present invention

| | Th17 | | | Treg | | |
|---|---|---|---|---|---|---|
| TCR condition | A | B | C | A | B | C |
| Control group | 2 | 3.4 | 1.1 | 2.6 | 3.3 | 2.8 |
| SD-281 | 1.2 | 1.5 | 0.8 | 2 | 4.6 | 2.8 |
| SD-282 | 1.2 | 1.5 | 0.9 | 2.5 | 4.6 | 2.9 |
| SD-283 | 1.1 | 2.3 | 0.5 | 3 | 5.1 | 3.3 |

A: Normal mouse cells,
B: Rheumatoid arthritis cells,
C: Lupus cells

TABLE 9

Analysis of effect on Th17 in Th17 differentiation condition of compounds according to the present invention

| Th17 condition | Th17 A |
|---|---|
| Control group | 5.7 |
| SD-281 | 0.4 |
| SD-282 | 0.5 |
| SD-283 | 0.9 |
| SD-284 | 2 |

Experimental Example 4

Analysis Result of Regulatory Activity of Th17 and Treg Cells

The inventors performed an analysis of inhibition of Th17 cells and induction activity of Treg cells disclosed in the <5> in order to examine whether the novel compounds of the present invention may simultaneously regulate differentiation and activity of the Treg cells having immunoregulatory ability in addition to differentiation and activity of the Th17 cells secreting IL-17 as the inflammatory cytokine.

As the analyzed result, the novel compounds of the present invention have the activity of decreasing the IL-17 expression in disease cells in the Th17 differentiation condition and inhibiting the differentiation to the Th17 cells as the disease cells and simultaneously increase the expression of Foxp3 which is a marker of immunoregulatory cells under the Treg condition and the number of Foxp3 expression cells. Further, it can be seen that the novel compounds of the present invention may effectively inhibit the hyperactivated Th17 cells.

Accordingly, through the results, it can be seen that the inventors can determine that the novel compounds of the present invention do not separately regulate the Th17 and the Treg, but simultaneously regulate the Th17 and the Treg to more effectively induce the immunoregulatory function, and thus it can be seen that these compounds can be used as a more effective immunoregulatory agent or immune disease treating agent.

Experimental Example 5

Analysis Result of Inhibition of Differentiation of Osteoclasts

The inventors verified the inhibition degree of the differentiation of osteoclasts by the compounds of the present invention in the cells stimulated by M-CSF and RANKL through straining of TRAP which is an osteoclast differentiation factor, in order to verify whether the novel compounds of the present invention may effectively treat the immune diseases.

As the analyzed result, the novel compounds of the present invention decrease the number of cells in which the TRAP which is the osteoclast differentiation factor is expressed. Through the result, it can be seen that the novel compounds of the present invention effectively decrease the differentiation of the osteoclasts that cause joint destruction to be effectively used for preventing and treating the disease due to the differentiation of the osteoclasts.

TABLE 10

Analysis of effect on inhibition of differentiation of osteoclasts of compounds according to the present invention

| | TRAP + Cell | |
|---|---|---|
| | A | B |
| Control group | 310 | 246 |
| SD-281 | 196 | 57 |
| SD-282 | 157 | 89 |
| SD-283 | 123 | 85 |

A: Normal mouse cells,
B: Rheumatoid arthritis cells

Experimental Example 6

Effect of Inhibiting Production of TNF-α and IL-17 as Inflammatory Cytokines by Targeting Spleen Cells of Mouse Furthermore, the inventors verified that inhibition degree of IL-17 and TNF-α as the inflammatory cytokines through an ELISA after treating anti mouse CD3 at a concentration of 0.5 μg/ml in the cells obtained from the spleen of a DBA1/J normal mouse group and commonly stimulating each compound at a concentration of 200 and 500 μM, in order to evaluating efficacy in an effect of inhibiting the inflammatory cytokines by targeting the compounds synthesized in Examples of the present invention.

As a result, as illustrated in FIG. 24, it can be seen that the compounds of SD-563, SD-564, SD-566, SD-567, SD-573, SD-574, and SD-580 have the activity capable of simultaneously inhibiting the IL-17 and the TNF-α as the inflammatory cytokines and the inhibition efficacy is increased to be concentration dependent.

For now, the present invention has been described with reference to the exemplary embodiments. It is understood to those skilled in the art that the present invention may be implemented as a modified form without departing from an essential characteristic of the present invention. Therefore, the disclosed exemplary embodiments should be considered from not a limitative viewpoint but an explanatory viewpoint. The scope of the present invention is described in not the above description but the appended claims, and it should be analyzed that all differences within the scope equivalent thereto are included in the present invention.

The invention claimed is:

1. A method of treating immune diseases in a mammalian in need thereof, comprising administering a therapeutically effective amount of N-ethyl-N-(4-fluorophenyl)-biguanide or a pharmaceutically acceptable salt thereof to the mammalian.

2. The method of claim 1, wherein the N-ethyl-N-(4-fluorophenyl)-biguanide or a pharmaceutically acceptable salt thereof decreases or inhibits production of inflammatory cytokines, inhibits production of auto-antibodies, and inhibits differentiation of osteoclasts.

3. The method of claim 2, wherein the inflammatory cytokine is IL-17, IL-6, TNF-α, IFN-γ, MMP-9, or STAT-3.

4. The method of claim 2, wherein the autoantibody is IgG, IgG1, or IgG2a.

5. The method of claim 1, wherein the N-ethyl-N-(4-fluorophenyl)-biguanide or a pharmaceutically acceptable salt thereof promotes or increases activity of regulatory T cells and decreases or inhibits activity of Th17 cells as pathological cells.

6. The method of claim 1, wherein the immune disease is selected from the group consisting of autoimmune diseases; inflammatory diseases; and transplantation rejection diseases.

7. The method of claim 6, wherein the autoimmune disease is selected from rheumatoid arthritis, Behcet's disease, multiple myositis or skin myositis, autoimmune hematocytopenia, autoimmune myocarditis, atopic dermatitis, asthma, primary cirrhosis, dermatomyositis, Goodpasture syndrome, autoimmune meningitis, sjogren's syndrome, lupus, Addison's disease, alopecia areata, ankylosing myelitis, autoimmune hepatitis, autoimmune mumps, Crohn's disease, insulin-dependent diabetes, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, sarcoidosis, scleroderma, vasculitis, vitiligo, myxedema, pernicious anemia, and ulcerative colitis.

8. The method of claim 6, wherein the transplantation rejection disease is a graft versus host disease.

* * * * *